(12) United States Patent
Gross

(10) Patent No.: US 11,400,299 B1
(45) Date of Patent: Aug. 2, 2022

(54) FLEXIBLE ANTENNA FOR STIMULATOR

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

(21) Appl. No.: 17/474,596

(22) Filed: Sep. 14, 2021

(51) Int. Cl.
*A61N 1/372* (2006.01)
*A61N 1/05* (2006.01)
*H02J 50/20* (2016.01)
*A61N 1/375* (2006.01)
*A61N 1/378* (2006.01)

(52) U.S. Cl.
CPC ....... *A61N 1/37229* (2013.01); *A61N 1/0558* (2013.01); *A61N 1/3754* (2013.01); *A61N 1/3787* (2013.01); *A61N 1/37518* (2017.08); *H02J 50/20* (2016.02)

(58) Field of Classification Search
CPC ............. A61N 1/37229; A61N 1/0558; A61N 1/37518; A61N 1/3754; A61N 1/3787; H02J 50/20
See application file for complete search history.

(56) References Cited

U.S. PATENT DOCUMENTS

| | | |
|---|---|---|
| 3,411,507 A | 11/1968 | Wingrove |
| 3,650,277 A | 3/1972 | Sjostrand et al. |
| 3,661,148 A | 5/1972 | Kolin |
| 3,693,625 A | 9/1972 | Auphan |
| 3,727,616 A | 4/1973 | Lenzkes |
| 4,019,518 A | 4/1977 | Maurer et al. |
| 4,154,227 A | 5/1979 | Krause et al. |
| 4,201,219 A | 5/1980 | Bozal |
| 4,338,945 A | 7/1982 | Kosugi et al. |
| 4,392,496 A | 7/1983 | Stanton |
| 4,474,630 A | 10/1984 | Planck et al. |
| 4,535,785 A | 8/1985 | Van Den Honert |
| 4,559,948 A | 12/1985 | Liss et al. |
| 4,573,481 A | 3/1986 | Bullara |
| 4,585,005 A | 4/1986 | Lue et al. |

(Continued)

FOREIGN PATENT DOCUMENTS

| | | |
|---|---|---|
| CN | 101048194 | 10/2007 |
| CN | 101500643 | 8/2009 |

(Continued)

OTHER PUBLICATIONS

C. de Balthasar, G. Cosendai, M. Hansen, D. Canfield, L. Chu, R. Davis, and J. Schulman, "Attachment of leads to RF-BION® microstimulators."Jul. 2005.

(Continued)

*Primary Examiner* — Eugene T Wu
(74) *Attorney, Agent, or Firm* — Sughrue Mion, PLLC

(57) ABSTRACT

An implant includes a housing that houses circuitry that is electrically coupled to one or more electrodes. The implant includes an antenna that is electrically coupled to the circuitry. The antenna has a pre-treatment state in which the antenna is not shaped to receive wireless power for treating a subject, and a treatment state in which the antenna is shaped to receive wireless power and to anchor the implant with respect to a nerve of the subject. Other embodiments are also described.

9 Claims, 14 Drawing Sheets

(56) References Cited

U.S. PATENT DOCUMENTS

| | | |
|---|---|---|
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,692,148 A | 9/1987 | Kantrowitz et al. |
| 4,739,764 A | 4/1988 | Lau |
| 4,791,931 A | 12/1988 | Slate |
| 4,808,157 A | 2/1989 | Coombs |
| 4,809,681 A | 3/1989 | Kantrowitz et al. |
| 4,821,723 A | 4/1989 | Baker, Jr. et al. |
| 4,848,352 A | 7/1989 | Pohndorf |
| 4,867,164 A | 9/1989 | Zabara |
| 4,926,865 A | 5/1990 | Oman |
| 4,938,766 A | 7/1990 | Jarvik |
| 4,962,751 A | 10/1990 | Krauter |
| 5,025,807 A | 6/1991 | Zabara |
| 5,036,854 A | 8/1991 | Schollmeyer et al. |
| 5,052,407 A | 10/1991 | Hauser et al. |
| 5,069,680 A | 12/1991 | Grandjean |
| 5,178,161 A | 1/1993 | Kovacs |
| 5,188,104 A | 2/1993 | Wernicke |
| 5,192,271 A | 3/1993 | Kalb et al. |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,224,491 A | 7/1993 | Mehra |
| 5,263,480 A | 11/1993 | Wernicke |
| 5,265,011 A | 11/1993 | O'Rourke |
| 5,265,601 A | 11/1993 | Mehra |
| 5,282,468 A | 2/1994 | Klepinski |
| 5,284,479 A | 2/1994 | De Jong |
| 5,292,344 A | 3/1994 | Douglas |
| 5,299,569 A | 4/1994 | Wernicke |
| 5,306,292 A | 4/1994 | Lindegren |
| 5,314,495 A | 5/1994 | Kovacs |
| 5,324,323 A | 6/1994 | Bui |
| 5,330,507 A | 7/1994 | Schwartz |
| 5,335,657 A | 8/1994 | Terry, Jr. |
| 5,344,439 A | 9/1994 | Otten |
| 5,372,573 A | 12/1994 | Habib |
| 5,411,031 A | 5/1995 | Yomtov |
| 5,411,535 A | 5/1995 | Fujii et al. |
| 5,423,871 A | 6/1995 | Hoegnelid et al. |
| 5,423,872 A | 6/1995 | Cigaina |
| 5,439,938 A | 8/1995 | Synder et al. |
| 5,454,840 A | 10/1995 | Krakovsky et al. |
| 5,458,626 A | 10/1995 | Krause |
| 5,487,760 A | 1/1996 | Villafana |
| 5,505,201 A | 4/1996 | Grill, Jr. |
| 5,509,924 A | 4/1996 | Paspa et al. |
| 5,540,730 A | 7/1996 | Terry, Jr. |
| 5,540,733 A | 7/1996 | Testerman et al. |
| 5,540,734 A | 7/1996 | Zabara |
| 5,549,655 A | 8/1996 | Erickson |
| 5,571,150 A | 11/1996 | Wernicke |
| 5,591,216 A | 1/1997 | Testerman et al. |
| 5,612,314 A | 3/1997 | Stamler et al. |
| 5,634,462 A | 6/1997 | Tyler et al. |
| 5,634,899 A | 6/1997 | Shapland et al. |
| 5,645,839 A | 7/1997 | Chobanian et al. |
| 5,649,966 A | 7/1997 | Noren et al. |
| 5,651,378 A | 7/1997 | Matheny et al. |
| 5,669,924 A | 9/1997 | Shaknovich |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,735,887 A | 4/1998 | Barreras et al. |
| 5,755,750 A | 5/1998 | Petruska |
| 5,762,599 A | 6/1998 | Sohn |
| 5,766,232 A | 6/1998 | Grevious et al. |
| 5,776,170 A | 7/1998 | MacDonald et al. |
| 5,776,171 A | 7/1998 | Peckham |
| 5,782,774 A | 7/1998 | Shmulewitz |
| 5,800,464 A | 9/1998 | Kieval |
| 5,800,502 A | 9/1998 | Boutos |
| 5,814,089 A | 9/1998 | Stokes |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,861,019 A | 1/1999 | Sun et al. |
| 5,873,865 A | 2/1999 | Horzewski et al. |
| 5,900,433 A | 5/1999 | Igo et al. |
| 5,902,712 A | 5/1999 | Burns et al. |
| 5,904,711 A | 5/1999 | Geddes et al. |
| 5,904,712 A | 5/1999 | Axelgaard |
| 5,906,641 A | 5/1999 | Thompson et al. |
| 5,913,876 A | 6/1999 | Taylor et al. |
| 5,916,239 A | 6/1999 | Geddes et al. |
| 5,925,061 A | 7/1999 | Ogi et al. |
| 5,935,077 A | 8/1999 | Ogle |
| 5,938,584 A | 8/1999 | Ardito et al. |
| 5,944,680 A | 8/1999 | Christopherson |
| 5,948,006 A | 9/1999 | Mann |
| 5,954,758 A | 9/1999 | Peckham |
| 5,967,986 A | 10/1999 | Cimochowski et al. |
| 5,991,664 A | 11/1999 | Seligman |
| 5,994,444 A | 11/1999 | Trescony et al. |
| 5,997,563 A | 12/1999 | Kretzers |
| 6,002,964 A | 12/1999 | Feler et al. |
| 6,014,589 A | 1/2000 | Farley et al. |
| 6,023,640 A | 2/2000 | Ross |
| 6,026,326 A | 2/2000 | Bardy |
| 6,026,328 A | 2/2000 | Peckham |
| 6,029,091 A | 2/2000 | De la Rama et al. |
| 6,032,076 A | 2/2000 | Melvin et al. |
| 6,038,485 A | 3/2000 | Axelgaard |
| 6,053,873 A | 4/2000 | Govari |
| 6,058,331 A | 5/2000 | King et al. |
| 6,066,163 A | 5/2000 | John |
| 6,071,274 A | 6/2000 | Thompson et al. |
| 6,073,048 A | 6/2000 | Kieval et al. |
| 6,091,992 A | 6/2000 | Bourgeois |
| 6,083,249 A | 7/2000 | Familoni |
| 6,086,525 A | 7/2000 | Davey et al. |
| 6,086,527 A | 7/2000 | Talpade |
| 6,091,977 A | 7/2000 | Tarjan et al. |
| 6,094,598 A | 7/2000 | Elsberry et al. |
| 6,097,984 A | 8/2000 | Douglas |
| 6,104,955 A | 8/2000 | Bourgeois |
| 6,104,956 A | 8/2000 | Naritoku et al. |
| 6,104,960 A | 8/2000 | Duysens et al. |
| 6,106,477 A | 8/2000 | Miesel et al. |
| 6,119,516 A | 9/2000 | Hock |
| 6,120,520 A | 9/2000 | Saadat |
| 6,141,587 A | 10/2000 | Mower |
| 6,146,335 A | 11/2000 | Gozani |
| 6,148,232 A | 11/2000 | Avrahami |
| 6,161,048 A | 12/2000 | Sluijter et al. |
| 6,169,924 B1 | 1/2001 | Meloy et al. |
| 6,178,349 B1 | 1/2001 | Kieval |
| 6,200,259 B1 | 3/2001 | March |
| 6,201,991 B1 | 3/2001 | Chekanov |
| 6,205,359 B1 | 3/2001 | Boveja |
| 6,212,435 B1 | 4/2001 | Lattner et al. |
| 6,214,032 B1 | 4/2001 | Loeb et al. |
| 6,230,061 B1 | 5/2001 | Hartung |
| 6,231,516 B1 | 5/2001 | Keilman et al. |
| 6,240,316 B1 | 5/2001 | Richmond |
| 6,245,103 B1 | 6/2001 | Stinson |
| 6,246,911 B1 | 6/2001 | Seligman |
| 6,246,912 B1 | 6/2001 | Sluijter et al. |
| 6,266,564 B1 | 7/2001 | Schwartz |
| 6,270,524 B1 | 8/2001 | Kim |
| 6,272,383 B1 | 8/2001 | Grey |
| 6,273,910 B1 | 8/2001 | Limon |
| 6,277,078 B1 | 8/2001 | Porat et al. |

(56) References Cited

U.S. PATENT DOCUMENTS

| | | |
|---|---|---|
| 6,280,377 B1 | 8/2001 | Talpade |
| 6,292,695 B1 | 9/2001 | Webster et al. |
| 6,292,703 B1 | 9/2001 | Meier et al. |
| 6,317,631 B1 | 11/2001 | Ben-Haim et al. |
| 6,319,241 B1 | 11/2001 | King |
| 6,332,089 B1 | 12/2001 | Acker |
| 6,339,725 B1 | 1/2002 | Naritoku et al. |
| 6,341,236 B1 | 1/2002 | Osorio et al. |
| 6,345,202 B2 | 2/2002 | Richmond et al. |
| 6,347,247 B1 | 2/2002 | Dev et al. |
| 6,356,784 B1 | 3/2002 | Lozano et al. |
| 6,356,788 B2 | 3/2002 | Boveja |
| 6,366,813 B1 | 4/2002 | Dilorenzo |
| 6,405,079 B1 | 6/2002 | Ansarinia |
| 6,411,845 B1 | 6/2002 | Mower |
| 6,418,348 B1 | 7/2002 | Witte |
| 6,423,084 B1 | 7/2002 | Germain |
| 6,432,991 B1 | 8/2002 | Thomas |
| 6,440,059 B1 | 8/2002 | Haas et al. |
| 6,442,432 B2 | 8/2002 | Lee |
| 6,445,953 B1 | 9/2002 | Bulkes et al. |
| 6,449,507 B1 | 9/2002 | Hill et al. |
| 6,456,878 B1 | 9/2002 | Yerich et al. |
| 6,463,323 B1 | 10/2002 | Conrad et al. |
| 6,463,328 B1 | 10/2002 | John |
| 6,473,644 B1 | 10/2002 | Terry, Jr. et al. |
| 6,480,747 B2 | 11/2002 | Schmidt |
| 6,485,524 B2 | 11/2002 | Strecker |
| 6,493,585 B2 | 12/2002 | Plicchi et al. |
| 6,496,729 B2 | 12/2002 | Thompson |
| 6,496,730 B1 | 12/2002 | Kleckner et al. |
| 6,496,732 B1 | 12/2002 | Wallace |
| 6,522,926 B1 | 2/2003 | Kieval et al. |
| 6,532,388 B1 | 3/2003 | Hill et al. |
| 6,575,994 B1 | 6/2003 | Marin et al. |
| 6,582,441 B1 | 6/2003 | He et al. |
| 6,582,461 B1 | 6/2003 | Burmeister et al. |
| 6,591,139 B2 | 7/2003 | Loftin et al. |
| 6,600,954 B2 | 7/2003 | Cohen |
| 6,600,956 B2 | 7/2003 | Maschino et al. |
| 6,606,521 B2 | 8/2003 | Paspa et al. |
| 6,610,713 B2 | 8/2003 | Tracey |
| 6,611,715 B1 | 8/2003 | Boveja |
| 6,615,085 B1 | 9/2003 | Boveja |
| 6,616,613 B1 | 9/2003 | Goodman |
| 6,616,624 B1 | 9/2003 | Kieval et al. |
| 6,618,627 B2 | 9/2003 | Lattner et al. |
| 6,622,041 B2 | 9/2003 | Terry, Jr. et al. |
| 6,626,935 B1 | 9/2003 | Ainsworth et al. |
| 6,631,296 B1 | 10/2003 | Parramon et al. |
| 6,632,991 B2 | 10/2003 | Chen |
| 6,641,542 B2 | 11/2003 | Cho et al. |
| 6,647,287 B1 | 11/2003 | Peel, III |
| 6,656,960 B2 | 12/2003 | Puskas |
| 6,668,191 B1 | 12/2003 | Boveja |
| 6,682,480 B1 | 1/2004 | Habib et al. |
| 6,712,772 B2 | 3/2004 | Cohen et al. |
| 6,721,603 B2 | 4/2004 | Zabara et al. |
| 6,735,474 B1 | 5/2004 | Loeb et al. |
| 6,735,475 B1 | 5/2004 | Whitehurst et al. |
| 6,770,022 B2 | 8/2004 | Mechlenburg |
| 6,770,088 B1 | 8/2004 | Jang |
| 6,788,973 B2 | 9/2004 | Davis et al. |
| 6,788,975 B1 | 9/2004 | Whitehurst et al. |
| 6,804,561 B2 | 10/2004 | Stover |
| 6,810,286 B2 | 10/2004 | Donovan et al. |
| 6,824,561 B2 | 11/2004 | Soykan et al. |
| 6,829,508 B2 | 12/2004 | Schulman |
| 6,839,594 B2 | 1/2005 | Cohen |
| 6,845,267 B2 | 1/2005 | Harrison et al. |
| 6,850,801 B2 | 2/2005 | Kieval et al. |
| 6,865,416 B2 | 3/2005 | Dev et al. |
| 6,871,092 B2 | 3/2005 | Piccone |
| 6,885,895 B1 | 4/2005 | Whitehurst et al. |
| 6,892,098 B2 | 5/2005 | Ayal |
| 6,907,295 B2 | 6/2005 | Gross et al. |
| 6,909,917 B2 | 6/2005 | Woods et al. |
| 6,934,583 B2 | 8/2005 | Weinberg et al. |
| 6,939,345 B2 | 9/2005 | KenKnight et al. |
| 6,947,792 B2 | 9/2005 | Ben-Haim et al. |
| 6,950,706 B2 | 9/2005 | Rodriguez et al. |
| 6,957,107 B2 | 10/2005 | Rogers et al. |
| 6,985,774 B2 | 1/2006 | Kieval et al. |
| 6,993,384 B2 | 1/2006 | Bradley et al. |
| 7,015,769 B2 | 3/2006 | Schulman et al. |
| 7,025,730 B2 | 4/2006 | Cho et al. |
| 7,027,860 B2 | 4/2006 | Bruninga et al. |
| 7,044,981 B2 | 5/2006 | Liu et al. |
| 7,047,076 B1 | 5/2006 | Li et al. |
| 7,054,689 B1 | 5/2006 | Whitehurst et al. |
| 7,054,692 B1 | 5/2006 | Whitehurst et al. |
| 7,062,318 B2 | 6/2006 | Ben-Haim et al. |
| 7,070,583 B1 | 7/2006 | Higuchi et al. |
| 7,076,307 B2 | 7/2006 | Boveja et al. |
| 7,079,901 B1 | 7/2006 | Loftin et al. |
| 7,082,336 B2 | 7/2006 | Ransbury et al. |
| 7,090,648 B2 | 8/2006 | Sackner et al. |
| 7,110,820 B2 | 9/2006 | Tcheng et al. |
| 7,123,961 B1 | 10/2006 | Kroll et al. |
| 7,149,574 B2 | 12/2006 | Yun et al. |
| 7,149,575 B2 | 12/2006 | Ostroff et al. |
| 7,151,914 B2 | 12/2006 | Brewer |
| 7,158,832 B2 | 1/2007 | Kieval et al. |
| 7,167,751 B1 | 1/2007 | Whitehurst et al. |
| 7,174,218 B1 | 2/2007 | Kuzma |
| 7,177,690 B2 | 2/2007 | Woods et al. |
| 7,177,698 B2 | 2/2007 | Klosterman et al. |
| 7,190,998 B2 | 3/2007 | Shalev et al. |
| 7,191,007 B2 | 3/2007 | Desai et al. |
| 7,191,012 B2 | 3/2007 | Boveja et al. |
| 7,201,719 B2 | 4/2007 | Feliss et al. |
| 7,203,549 B2 | 4/2007 | Schommer et al. |
| 7,206,637 B2 | 4/2007 | Salo |
| 7,209,792 B1 | 4/2007 | Parramon et al. |
| 7,212,867 B2 | 5/2007 | Venrooij et al. |
| 7,216,000 B2 | 5/2007 | Sieracki et al. |
| 7,225,019 B2 | 5/2007 | Jahns et al. |
| 7,225,032 B2 | 5/2007 | Schmeling et al. |
| 7,228,167 B2 | 6/2007 | Kara et al. |
| 7,228,178 B2 | 6/2007 | Carroll |
| 7,229,403 B2 | 6/2007 | Schock et al. |
| 7,239,921 B2 | 7/2007 | Canfield et al. |
| 7,242,982 B2 | 7/2007 | Singhal et al. |
| 7,254,449 B2 | 8/2007 | Karunasiri |
| 7,263,402 B2 | 8/2007 | Thacker et al. |
| 7,263,405 B2 | 8/2007 | Boveja et al. |
| 7,269,457 B2 | 9/2007 | Shafer et al. |
| 7,277,748 B2 | 10/2007 | Wingeier et al. |
| 7,277,749 B2 | 10/2007 | Gordon et al. |
| 7,277,761 B2 | 10/2007 | Shelchuk |
| 7,286,880 B2 | 10/2007 | Olson et al. |
| 7,286,881 B2 | 10/2007 | Schommer et al. |
| 7,289,853 B1 | 10/2007 | Campbell et al. |
| 7,291,113 B2 | 11/2007 | Satoh et al. |
| 7,292,886 B1 | 11/2007 | Kroll |
| 7,292,890 B2 | 11/2007 | Whitehurst et al. |
| 7,299,091 B2 | 11/2007 | Barrett et al. |
| 7,308,316 B2 | 12/2007 | Schommer |
| 7,321,793 B2 | 1/2008 | Ben Ezra et al. |
| 7,324,852 B2 | 1/2008 | Barolat et al. |
| 7,324,853 B2 | 1/2008 | Ayal |
| 7,330,756 B2 | 2/2008 | Mandeldt |
| 7,337,007 B2 | 2/2008 | Nathan et al. |
| 7,342,508 B2 | 3/2008 | Morgan et al. |
| 7,363,076 B2 | 4/2008 | Yun et al. |
| 7,363,087 B2 | 4/2008 | Nghiem et al. |
| 7,367,970 B2 | 5/2008 | Govari et al. |
| 7,376,466 B2 | 5/2008 | He et al. |
| 7,389,145 B2 | 6/2008 | Kilgore et al. |
| 7,389,149 B2 | 6/2008 | Rossing et al. |
| 7,395,119 B2 | 7/2008 | Hagen et al. |
| 7,403,823 B1 | 7/2008 | Kroll et al. |
| 7,444,183 B2 | 10/2008 | Knudson et al. |
| 7,452,334 B2 | 11/2008 | Gianchandani |

(56) References Cited

U.S. PATENT DOCUMENTS

| | | |
|---|---|---|
| 7,471,986 B2 | 12/2008 | Hatlestad |
| 7,476,200 B2 | 1/2009 | Tal |
| 7,480,532 B2 | 1/2009 | Kieval et al. |
| 7,483,748 B2 | 1/2009 | Torgerson et al. |
| 7,483,752 B2 | 1/2009 | Von arx et al. |
| 7,486,991 B2 | 2/2009 | Libbus et al. |
| 7,489,561 B2 | 2/2009 | Armstrong et al. |
| 7,499,747 B2 | 3/2009 | Kieval et al. |
| 7,499,748 B2 | 3/2009 | Moffitt et al. |
| 7,502,650 B2 | 3/2009 | Kieval |
| 7,502,652 B2 | 3/2009 | Gaunt et al. |
| 7,515,012 B2 | 4/2009 | Schulman et al. |
| 7,515,967 B2 | 4/2009 | Phillips et al. |
| 7,519,421 B2 | 4/2009 | Denker et al. |
| 7,532,932 B2 | 5/2009 | Denker et al. |
| 7,536,226 B2 | 5/2009 | Williams |
| 7,539,538 B2 | 5/2009 | Parramon et al. |
| 7,555,344 B2 | 6/2009 | Maschino et al. |
| 7,561,918 B2 | 7/2009 | Armstrong et al. |
| 7,561,921 B2 | 7/2009 | Phillips et al. |
| 7,565,204 B2 | 7/2009 | Matei |
| 7,570,999 B2 | 8/2009 | Libbus et al. |
| 7,613,511 B2 | 11/2009 | Wu et al. |
| 7,613,515 B2 | 11/2009 | Knudson et al. |
| 7,614,998 B2 | 11/2009 | Gross et al. |
| 7,616,997 B2 | 11/2009 | Kieval et al. |
| 7,617,003 B2 | 11/2009 | Caparso et al. |
| 7,623,926 B2 | 11/2009 | Rossing et al. |
| 7,628,750 B2 | 12/2009 | Cohen |
| 7,630,771 B2 | 12/2009 | Cauller |
| 7,634,313 B1 | 12/2009 | Kroll et al. |
| 7,634,315 B2 | 12/2009 | Cholette |
| 7,643,147 B2 | 1/2010 | Pless |
| 7,647,117 B2 | 1/2010 | Bauhahn |
| 7,650,192 B2 | 1/2010 | Wahlstrand |
| 7,655,014 B2 | 2/2010 | Ko et al. |
| 7,657,311 B2 | 2/2010 | Bardy et al. |
| 7,657,317 B2 | 2/2010 | Thacker et al. |
| 7,657,322 B2 | 2/2010 | Bardy et al. |
| 7,660,632 B2 | 2/2010 | Kirby et al. |
| 7,680,538 B2 | 3/2010 | Durand et al. |
| 7,680,540 B2 | 3/2010 | Jensen et al. |
| 7,706,875 B2 | 4/2010 | Buras et al. |
| 7,706,884 B2 | 4/2010 | Libbus |
| 7,706,886 B2 | 4/2010 | Morimoto et al. |
| 7,711,434 B2 | 5/2010 | Denker et al. |
| 7,715,915 B1 | 5/2010 | Ryu et al. |
| 7,720,547 B2 | 5/2010 | Denker et al. |
| 7,725,194 B2 | 5/2010 | Klostermann et al. |
| 7,736,379 B2 | 6/2010 | Ewers et al. |
| 7,738,961 B2 | 6/2010 | Sharma |
| 7,747,302 B2 | 6/2010 | Milledge |
| 7,747,325 B2 | 6/2010 | Dilorenzo |
| 7,765,000 B2 | 7/2010 | Zhang et al. |
| 7,765,008 B2 | 7/2010 | Ben-Haim et al. |
| 7,769,446 B2 | 8/2010 | Moffitt et al. |
| 7,780,625 B2 | 8/2010 | Bardy |
| 7,780,719 B2 | 8/2010 | Killion et al. |
| 7,797,050 B2 | 9/2010 | Libbus et al. |
| 7,801,602 B2 | 9/2010 | McClure et al. |
| 7,801,604 B2 | 9/2010 | Brockway et al. |
| 7,803,142 B2 | 9/2010 | Longson et al. |
| 7,809,437 B2 | 10/2010 | Palmer et al. |
| 7,811,221 B2 | 10/2010 | Gross |
| 7,813,805 B1 | 10/2010 | Farazi |
| 7,813,812 B2 | 10/2010 | Kieval et al. |
| 7,817,280 B2 | 10/2010 | Pless |
| 7,822,480 B2 | 10/2010 | Park et al. |
| 7,826,899 B1 | 11/2010 | Ryu et al. |
| 7,840,282 B2 | 11/2010 | Williams et al. |
| 7,848,818 B2 | 12/2010 | Barolat et al. |
| 7,848,820 B2 | 12/2010 | Abrahamson |
| 7,856,273 B2 | 12/2010 | Maschino et al. |
| 7,860,566 B2 | 12/2010 | Mazgalev et al. |
| 7,869,867 B2 | 1/2011 | Armstrong et al. |
| 7,869,870 B1 | 1/2011 | Farazi |
| 7,881,782 B2 | 2/2011 | Libbus et al. |
| 7,881,792 B1 | 2/2011 | Farazi |
| 7,894,902 B2 | 2/2011 | Rom et al. |
| 7,894,905 B2 | 2/2011 | Pless et al. |
| 7,899,547 B1 | 3/2011 | Emadi et al. |
| 7,899,554 B2 | 3/2011 | Williams et al. |
| 7,899,556 B2 | 3/2011 | Nathan et al. |
| 7,904,171 B2 | 3/2011 | Parramon et al. |
| 7,912,551 B2 | 3/2011 | Wosmek |
| 7,925,350 B1 | 4/2011 | Palmer |
| 7,917,226 B2 | 5/2011 | Nghiem |
| 7,937,148 B2 | 5/2011 | Jacobson |
| 7,941,218 B2 | 5/2011 | Sambelashvili et al. |
| 7,949,400 B2 | 5/2011 | Kieval et al. |
| 7,962,211 B2 | 6/2011 | Torgerson et al. |
| 7,962,220 B2 | 6/2011 | Kolafa et al. |
| 7,974,706 B2 | 7/2011 | Moffitt et al. |
| 7,979,126 B2 | 7/2011 | Payne et al. |
| 7,991,467 B2 | 8/2011 | Markowitz et al. |
| 7,991,474 B2 | 8/2011 | Aldrich et al. |
| 7,996,079 B2 | 8/2011 | Armstrong |
| 7,996,089 B2 | 8/2011 | Haugland et al. |
| 7,996,092 B2 | 8/2011 | Mrva et al. |
| 8,005,547 B2 | 8/2011 | Forsberg et al. |
| 8,019,443 B2 | 9/2011 | Scheicher et al. |
| 8,046,085 B2 | 10/2011 | Knudson et al. |
| 8,050,771 B2 | 11/2011 | Yamamoto et al. |
| 8,055,336 B1 | 11/2011 | Schulman et al. |
| 8,055,350 B2 | 11/2011 | Roberts |
| 8,065,019 B2 | 11/2011 | Marnfeldt et al. |
| 8,075,556 B2 | 12/2011 | Betts |
| 8,086,313 B2 | 12/2011 | Singhal et al. |
| 8,086,314 B1 | 12/2011 | Kieval |
| 8,090,438 B2 | 1/2012 | Bardy et al. |
| 8,095,218 B2 | 1/2012 | Gross et al. |
| 8,115,448 B2 | 2/2012 | John |
| 8,121,692 B2 | 2/2012 | Haefner et al. |
| 8,127,424 B2 | 3/2012 | Haller et al. |
| 8,131,362 B2 | 3/2012 | Moffitt et al. |
| 8,131,377 B2 | 3/2012 | Shhi et al. |
| 8,140,168 B2 | 3/2012 | Olson et al. |
| 8,150,508 B2 | 4/2012 | Craig |
| 8,160,701 B2 | 4/2012 | Zhao et al. |
| 8,170,675 B2 | 5/2012 | Alataris et al. |
| 8,170,681 B2 | 5/2012 | Jimenez et al. |
| 8,175,705 B2 | 5/2012 | Libbus |
| 8,175,719 B2 | 5/2012 | Shi et al. |
| 8,177,792 B2 | 5/2012 | Lubock et al. |
| 8,185,207 B2 | 5/2012 | Molnar et al. |
| 8,209,021 B2 | 6/2012 | Alataris et al. |
| 8,224,437 B2 | 7/2012 | Kieval et al. |
| 8,224,453 B2 | 7/2012 | De Ridder |
| 8,229,567 B2 | 7/2012 | Phillips et al. |
| 8,244,367 B2 | 8/2012 | Wahlstrand et al. |
| 8,244,378 B2 | 8/2012 | Bly et al. |
| 8,249,705 B1 | 8/2012 | Kieval et al. |
| 8,255,057 B2 | 8/2012 | Fang et al. |
| 8,260,432 B2 | 9/2012 | DiGiore et al. |
| 8,265,770 B2 | 9/2012 | Toy et al. |
| 8,290,595 B2 | 10/2012 | Kieval et al. |
| 8,306,627 B2 | 11/2012 | Armstrong |
| 8,311,638 B2 | 11/2012 | Aghassian |
| 8,321,028 B1 | 11/2012 | Thenuwara et al. |
| 8,335,569 B2 | 12/2012 | Aghassian |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,267 B2 | 1/2013 | Schleicher et al. |
| 8,369,963 B2 | 2/2013 | Parramon et al. |
| 8,374,700 B2 | 2/2013 | Haubrich et al. |
| 8,386,038 B2 | 2/2013 | Bianchi et al. |
| 8,386,047 B2 | 2/2013 | Koester |
| 8,386,048 B2 | 2/2013 | McClure et al. |
| 8,391,970 B2 | 3/2013 | Tracey et al. |
| 8,396,559 B2 | 3/2013 | Alataris et al. |
| 8,406,868 B2 | 3/2013 | Buschman et al. |
| 8,428,731 B2 | 4/2013 | Armstrong |
| 8,428,744 B2 | 4/2013 | Stancer et al. |

(56) References Cited

U.S. PATENT DOCUMENTS

| | | |
|---|---|---|
| 8,428,746 B2 | 4/2013 | DiGiore et al. |
| 8,428,748 B2 | 4/2013 | Alataris et al. |
| 8,437,846 B2 | 5/2013 | Swoyer et al. |
| 8,437,853 B2 | 5/2013 | Inman et al. |
| 8,442,639 B2 | 5/2013 | Walker et al. |
| 8,449,472 B2 | 5/2013 | Ryu et al. |
| 8,457,743 B2 | 6/2013 | Gollasch et al. |
| 8,457,744 B2 | 6/2013 | Janzig et al. |
| 8,457,748 B2 | 6/2013 | Lange |
| 8,457,759 B2 | 6/2013 | Parker et al. |
| 8,463,392 B2 | 6/2013 | Aghassian |
| 8,463,404 B2 | 6/2013 | Levi et al. |
| 8,467,884 B2 | 6/2013 | Chen et al. |
| 8,473,066 B2 | 6/2013 | Aghassian et al. |
| 8,478,414 B2 | 7/2013 | Kieval et al. |
| 8,478,420 B2 | 7/2013 | Armstrong et al. |
| 8,483,838 B2 | 7/2013 | Nghiem et al. |
| 8,483,845 B2 | 7/2013 | Sage |
| 8,494,640 B2 | 7/2013 | Peterson et al. |
| 8,494,650 B2 | 7/2013 | Glukhovsky et al. |
| 8,497,804 B2 | 7/2013 | Haubrich et al. |
| 8,498,704 B2 | 7/2013 | Shuros et al. |
| 8,498,716 B2 | 7/2013 | Chen et al. |
| 8,504,161 B1 | 8/2013 | Kornet et al. |
| 8,509,905 B2 | 8/2013 | Alataris et al. |
| 8,509,906 B2 | 8/2013 | Walker et al. |
| 8,509,919 B2 | 8/2013 | Yoo et al. |
| 8,515,558 B1 | 8/2013 | Zweber et al. |
| 8,521,293 B2 | 8/2013 | Anderson et al. |
| 8,538,535 B2 | 9/2013 | Gross |
| 8,538,542 B2 | 9/2013 | Knudson et al. |
| 8,538,548 B2 | 9/2013 | Shi et al. |
| 8,543,200 B2 | 9/2013 | Lane et al. |
| 8,554,326 B2 | 10/2013 | Alataris et al. |
| 8,555,894 B2 | 10/2013 | Schulman et al. |
| 8,560,076 B2 | 10/2013 | Kieval et al. |
| 8,571,651 B2 | 10/2013 | Ben-ezra et al. |
| 8,571,654 B2 | 10/2013 | Libbus et al. |
| 8,571,664 B2 | 10/2013 | Anderson et al. |
| 8,577,458 B1 | 11/2013 | Libbus et al. |
| 8,577,474 B2 | 11/2013 | Rahman et al. |
| 8,588,933 B2 | 11/2013 | Floyd et al. |
| 8,600,505 B2 | 12/2013 | Libbus et al. |
| 8,600,511 B2 | 12/2013 | Yared et al. |
| 8,600,521 B2 | 12/2013 | Armstrong et al. |
| 8,606,359 B2 | 12/2013 | Rossing et al. |
| 8,612,014 B2 | 12/2013 | Rahman et al. |
| 8,612,019 B2 | 12/2013 | Moffitt |
| 8,620,422 B2 | 12/2013 | Kieval et al. |
| 8,620,435 B2 | 12/2013 | Rooney et al. |
| 8,620,449 B2 | 12/2013 | Zhao et al. |
| 8,620,450 B2 | 12/2013 | Tockman et al. |
| 8,626,290 B2 | 1/2014 | Dagan |
| 8,626,299 B2 | 1/2014 | Gross et al. |
| 8,626,310 B2 | 1/2014 | Barror et al. |
| 8,630,709 B2 | 1/2014 | Libbus et al. |
| 8,634,927 B2 | 1/2014 | Olson et al. |
| 8,634,928 B1 | 1/2014 | O'Driscoll et al. |
| 8,639,327 B2 | 1/2014 | Zhou et al. |
| 8,639,339 B2 | 1/2014 | Bange et al. |
| 8,644,928 B2 | 2/2014 | Takata |
| 8,644,947 B2 | 2/2014 | Zhu et al. |
| 8,644,948 B2 | 2/2014 | Grevious et al. |
| 8,649,863 B2 | 2/2014 | Gross et al. |
| 8,649,874 B2 | 2/2014 | Alataris et al. |
| 8,660,655 B2 | 2/2014 | Peterson et al. |
| 8,660,666 B2 | 2/2014 | Craig |
| 8,663,103 B2 | 3/2014 | Causey et al. |
| 8,666,491 B2 | 3/2014 | Chen et al. |
| 8,666,504 B2 | 3/2014 | Dronov et al. |
| 8,670,835 B2 | 3/2014 | Park et al. |
| 8,676,337 B2 | 3/2014 | Kallmyer |
| 8,676,341 B2 | 3/2014 | Kane et al. |
| 8,688,232 B2 | 4/2014 | Finley et al. |
| 8,692,717 B2 | 4/2014 | Friedman |
| 8,694,108 B2 | 4/2014 | Alataris et al. |
| 8,694,109 B2 | 4/2014 | Alataris et al. |
| 8,700,145 B2 | 4/2014 | Kilgard et al. |
| 8,700,157 B2 | 4/2014 | Goetz et al. |
| 8,700,173 B2 | 4/2014 | Edlund |
| 8,706,223 B2 | 4/2014 | Zhou et al. |
| 8,712,531 B2 | 4/2014 | Kieval et al. |
| 8,712,533 B2 | 4/2014 | Alataris et al. |
| 8,712,534 B2 | 4/2014 | Wei |
| 8,718,780 B2 | 5/2014 | Lee |
| 8,718,781 B2 | 5/2014 | Alataris et al. |
| 8,718,782 B2 | 5/2014 | Alataris et al. |
| 8,729,129 B2 | 5/2014 | Tracey et al. |
| 8,731,663 B2 | 5/2014 | Bianchi et al. |
| 8,738,126 B2 | 5/2014 | Craig |
| 8,738,145 B2 | 5/2014 | Goetz et al. |
| 8,744,586 B2 | 6/2014 | Georgakopoulos et al. |
| 8,750,985 B2 | 6/2014 | Parramon et al. |
| 8,751,009 B2 | 6/2014 | Wacnik |
| 8,755,893 B2 | 6/2014 | Gross et al. |
| 8,755,907 B2 | 6/2014 | Kieval et al. |
| 8,761,895 B2 | 6/2014 | Stevenson et al. |
| 8,768,472 B2 | 7/2014 | Fang et al. |
| 8,774,912 B2 | 7/2014 | Gerber |
| 8,774,926 B2 | 7/2014 | Alataris et al. |
| 8,788,028 B2 | 7/2014 | Kumar et al. |
| 8,788,045 B2 | 7/2014 | Gross et al. |
| 8,788,066 B2 | 7/2014 | Cates et al. |
| 8,792,988 B2 | 7/2014 | Alataris et al. |
| 8,798,773 B2 | 8/2014 | Mashiach |
| 8,805,513 B2 | 8/2014 | Libbus |
| 8,805,519 B2 | 8/2014 | Parker et al. |
| 8,812,135 B2 | 8/2014 | Mashiach |
| 8,818,508 B2 | 8/2014 | Scheiner |
| 8,818,524 B2 | 8/2014 | Hincapie et al. |
| 8,843,203 B2 | 9/2014 | Lee et al. |
| 8,849,410 B2 | 9/2014 | Walker et al. |
| 8,849,412 B2 | 9/2014 | Perryman et al. |
| 8,855,783 B2 | 10/2014 | Dagan et al. |
| 8,862,239 B2 | 10/2014 | Alataris et al. |
| 8,862,243 B2 | 10/2014 | Gross |
| 8,868,192 B2 | 10/2014 | Alataris et al. |
| 8,874,217 B2 | 10/2014 | Alataris et al. |
| 8,874,219 B2 | 10/2014 | Trier et al. |
| 8,874,221 B2 | 10/2014 | Alataris et al. |
| 8,874,222 B2 | 10/2014 | Alataris et al. |
| 8,880,177 B2 | 11/2014 | Alataris et al. |
| 8,880,185 B2 | 11/2014 | Hastings et al. |
| 8,884,779 B2 | 11/2014 | Herman et al. |
| 8,886,326 B2 | 11/2014 | Alataris et al. |
| 8,886,327 B2 | 11/2014 | Alataris et al. |
| 8,886,328 B2 | 11/2014 | Alataris et al. |
| 8,892,209 B2 | 11/2014 | Alataris et al. |
| 8,892,214 B2 | 11/2014 | Bonde et al. |
| 8,903,497 B2 | 12/2014 | Norgaard et al. |
| 8,903,499 B2 | 12/2014 | Pless et al. |
| 8,918,179 B2 | 12/2014 | Peterson et al. |
| 8,918,180 B2 | 12/2014 | Peterson |
| 8,923,988 B2 | 12/2014 | Bradley |
| 8,929,990 B2 | 1/2015 | Moffitt et al. |
| 8,942,808 B2 | 1/2015 | Peterson et al. |
| 8,954,165 B2 | 2/2015 | Sharma et al. |
| 8,958,884 B2 | 2/2015 | Kothandaraman et al. |
| 8,958,891 B2 | 2/2015 | Kane et al. |
| 8,983,615 B2 | 3/2015 | Tahmasian et al. |
| 8,983,618 B2 | 3/2015 | Yamamoto et al. |
| 8,989,864 B2 | 3/2015 | Funderburk et al. |
| 8,989,868 B2 | 3/2015 | Mashiach et al. |
| 8,994,325 B2 | 3/2015 | Carbunaru et al. |
| 8,996,115 B2 | 3/2015 | Trier et al. |
| 9,002,445 B2 | 4/2015 | Chen |
| 9,002,460 B2 | 4/2015 | Parker |
| 9,002,461 B2 | 4/2015 | Walker et al. |
| 9,002,466 B2 | 4/2015 | Trier et al. |
| 9,005,106 B2 | 4/2015 | Gross et al. |
| 9,020,599 B2 | 4/2015 | Rooney et al. |
| 9,020,602 B2 | 4/2015 | Aghassian |
| 9,026,227 B2 | 5/2015 | Daglow |
| 9,030,159 B2 | 5/2015 | Chen et al. |

(56) References Cited

U.S. PATENT DOCUMENTS

| | | |
|---|---|---|
| 9,031,666 B2 | 5/2015 | Fell |
| 9,037,261 B2 | 5/2015 | Bradley |
| 9,042,997 B2 | 5/2015 | Rahman et al. |
| 9,044,616 B2 | 6/2015 | Chen et al. |
| 9,056,206 B2 | 6/2015 | Torgerson et al. |
| 9,061,140 B2 | 6/2015 | Shi et al. |
| 9,061,151 B2 | 6/2015 | Mashiach et al. |
| 9,061,159 B2 | 6/2015 | Rahman |
| 9,061,162 B2 | 6/2015 | Mashiach et al. |
| 9,067,072 B2 | 6/2015 | Tahmasian et al. |
| 9,070,507 B2 | 6/2015 | Dronov et al. |
| 9,072,896 B2 | 7/2015 | Dar et al. |
| 9,079,041 B2 | 7/2015 | Park et al. |
| 9,084,900 B2 | 7/2015 | Hershey et al. |
| 9,089,712 B2 | 7/2015 | Joshi et al. |
| 9,095,726 B2 | 8/2015 | Parramon et al. |
| 9,101,774 B2 | 8/2015 | Mashiach et al. |
| 9,119,969 B2 | 9/2015 | Vansickle |
| 9,142,989 B2 | 9/2015 | Fell et al. |
| 9,149,635 B2 | 10/2015 | Denison et al. |
| 9,149,643 B2 | 10/2015 | Tahmasian et al. |
| 9,154,219 B2 | 10/2015 | Polefko et al. |
| 9,155,899 B2 | 10/2015 | Mashiach et al. |
| 9,155,901 B2 | 10/2015 | Dearden et al. |
| 9,162,068 B2 | 10/2015 | Dronov |
| 9,174,051 B2 | 11/2015 | Marnfeldt et al. |
| 9,174,053 B2 | 11/2015 | Zhu |
| 9,186,504 B2 | 11/2015 | Gross |
| 9,192,770 B2 | 11/2015 | Wang et al. |
| 9,199,083 B2 | 12/2015 | Caparso et al. |
| 9,205,258 B2 | 12/2015 | Simon et al. |
| 9,211,418 B2 | 12/2015 | Aghassian |
| 9,216,297 B2 | 12/2015 | Kast et al. |
| 9,220,907 B2 | 12/2015 | Mashiach et al. |
| 9,220,909 B2 | 12/2015 | Carbunaru et al. |
| 9,220,910 B2 | 12/2015 | Colborn |
| 9,225,194 B2 | 12/2015 | Joshi |
| 9,227,075 B2 | 1/2016 | Aghassian et al. |
| 9,232,903 B2 | 1/2016 | Pless et al. |
| 9,238,138 B2 | 1/2016 | Lee et al. |
| 9,240,630 B2 | 1/2016 | Joshi |
| 9,242,106 B2 | 1/2016 | Klosterman et al. |
| 9,248,279 B2 | 2/2016 | Chen et al. |
| 9,248,292 B2 | 2/2016 | Trier et al. |
| 9,248,302 B2 | 2/2016 | Mashiach et al. |
| 9,254,393 B2 | 2/2016 | Perryman et al. |
| 9,259,571 B2 | 2/2016 | Straka et al. |
| 9,259,582 B2 | 2/2016 | Joshi et al. |
| 9,259,584 B2 | 2/2016 | Bauhahn et al. |
| 9,265,941 B2 | 2/2016 | Van Den Biggelaar et al. |
| 9,265,958 B2 | 2/2016 | Joshi et al. |
| 9,289,616 B2 | 3/2016 | Koester |
| 9,295,841 B2 | 3/2016 | Fang et al. |
| 9,295,850 B2 | 3/2016 | Kallmyer |
| 9,314,613 B2 | 4/2016 | Mashiach |
| 9,314,628 B2 | 4/2016 | North et al. |
| 9,314,642 B2 | 4/2016 | Ozawa et al. |
| 9,320,847 B2 | 4/2016 | Rooney et al. |
| 9,320,899 B2 | 4/2016 | Parramon et al. |
| 9,320,908 B2 | 4/2016 | Fletcher et al. |
| 9,333,367 B2 | 5/2016 | Chen |
| 9,339,660 B2 | 5/2016 | Feldman et al. |
| 9,343,923 B2 | 5/2016 | Joshi |
| 9,352,161 B2 | 5/2016 | Thacker et al. |
| 9,370,664 B2 | 6/2016 | Marnfeldt et al. |
| 9,375,582 B2 | 6/2016 | Kaula et al. |
| 9,381,360 B2 | 7/2016 | Hershey |
| 9,387,331 B2 | 7/2016 | Zhao et al. |
| 9,387,332 B2 | 7/2016 | Zhao et al. |
| 9,393,423 B2 | 7/2016 | Parramon et al. |
| 9,393,428 B2 | 7/2016 | Nyberg, II et al. |
| 9,393,435 B2 | 7/2016 | Mashiach |
| 9,398,901 B2 | 7/2016 | Tischendorf et al. |
| 9,399,130 B2 | 7/2016 | Bonde et al. |
| 9,399,131 B2 | 7/2016 | Digiore et al. |
| 9,399,143 B2 | 7/2016 | Yamamoto et al. |
| 9,403,013 B2 | 8/2016 | Walker et al. |
| 9,403,020 B2 | 8/2016 | Wingeier |
| 9,403,021 B2 | 8/2016 | Dronov |
| 9,407,110 B2 | 8/2016 | Lui et al. |
| 9,409,029 B2 | 8/2016 | Perryman et al. |
| 9,435,830 B2 | 9/2016 | Joshi |
| 9,446,251 B1 | 9/2016 | Perryman et al. |
| 9,446,254 B2 | 9/2016 | Ozawa et al. |
| 9,449,501 B2 | 9/2016 | Grevious et al. |
| 9,452,288 B2 | 9/2016 | Whitehurst et al. |
| 9,457,186 B2 | 10/2016 | Gross |
| 9,463,321 B2 | 10/2016 | Bradley et al. |
| 9,463,323 B2 | 10/2016 | Lee et al. |
| 9,463,326 B2 | 10/2016 | Ranu |
| 9,468,771 B2 | 10/2016 | Griffith et al. |
| 9,468,772 B2 | 10/2016 | Demmer |
| 9,469,437 B2 | 10/2016 | Kamath |
| 9,474,905 B2 | 10/2016 | Doan et al. |
| 9,480,841 B2 | 11/2016 | Hershey et al. |
| 9,504,832 B2 | 11/2016 | Libbus et al. |
| 9,504,838 B2 | 11/2016 | Rao et al. |
| 9,517,344 B1 | 12/2016 | Bradley |
| 9,517,352 B2 | 12/2016 | Kast et al. |
| 9,522,270 B2 | 12/2016 | Perryman et al. |
| 9,526,637 B2 | 12/2016 | Dagan et al. |
| 9,533,148 B2 | 1/2017 | Carcieri |
| 9,533,153 B2 | 1/2017 | Libbus et al. |
| 9,533,154 B2 | 1/2017 | Kothandaraman et al. |
| 9,533,162 B2 | 1/2017 | Ter-petrosyan et al. |
| 9,555,257 B2 | 1/2017 | Mashiach et al. |
| 9,561,365 B2 | 2/2017 | Shi et al. |
| 9,585,642 B2 | 3/2017 | Dinsmoor et al. |
| 9,586,054 B2 | 3/2017 | Aghassian |
| 9,592,385 B2 | 3/2017 | Kaula et al. |
| 9,597,516 B2 | 3/2017 | Lee et al. |
| 9,597,517 B2 | 3/2017 | Moffitt |
| 9,597,521 B2 | 3/2017 | Plotkin et al. |
| 9,610,450 B2 | 4/2017 | Zhao |
| 9,616,230 B2 | 4/2017 | Grandhe |
| 9,623,244 B2 | 4/2017 | Kothandaraman |
| 9,623,245 B2 | 4/2017 | King et al. |
| 9,623,253 B2 | 4/2017 | Perryman et al. |
| 9,623,257 B2 | 4/2017 | Olson et al. |
| 9,630,231 B2 | 4/2017 | Kelsch et al. |
| 9,636,508 B2 | 5/2017 | Chen et al. |
| 9,643,022 B2 | 5/2017 | Mashiach et al. |
| 9,649,049 B2 | 5/2017 | Pless et al. |
| 9,649,487 B2 | 5/2017 | Gross et al. |
| 9,649,493 B2 | 5/2017 | Mashiach |
| 9,653,941 B2 | 5/2017 | Dinsmoor et al. |
| 9,656,074 B2 | 5/2017 | Simon et al. |
| 9,656,076 B2 | 5/2017 | Trier et al. |
| 9,656,081 B2 | 5/2017 | Feldman et al. |
| 9,675,809 B2 | 6/2017 | Chow |
| 9,687,649 B2 | 6/2017 | Thacker |
| 9,700,725 B2 | 7/2017 | Zhu |
| 9,700,730 B2 | 7/2017 | Carbunaru et al. |
| 9,707,404 B2 | 7/2017 | Rao et al. |
| 9,713,707 B2 | 7/2017 | Oron et al. |
| 9,713,717 B2 | 7/2017 | Aghassian |
| 9,713,718 B2 | 7/2017 | Lamont et al. |
| 9,713,721 B2 | 7/2017 | Kothandaraman |
| 9,724,513 B2 | 8/2017 | Lane et al. |
| 9,731,116 B2 | 8/2017 | Chen |
| 9,737,703 B2 | 8/2017 | Carbunaru et al. |
| 9,737,714 B2 | 8/2017 | Zottola |
| 9,744,347 B2 | 8/2017 | Chen et al. |
| 9,744,362 B2 | 8/2017 | Steinke et al. |
| 9,744,365 B2 | 8/2017 | Davis et al. |
| 9,744,368 B2 | 8/2017 | Dinsmoor |
| 9,750,930 B2 | 9/2017 | Chen |
| 9,782,588 B2 | 10/2017 | Shi et al. |
| 9,782,593 B2 | 10/2017 | Parramon et al. |
| 9,782,596 B2 | 10/2017 | Vamos et al. |
| 9,789,314 B2 | 10/2017 | Perryman et al. |
| 9,789,321 B2 | 10/2017 | Dixit et al. |
| 9,789,324 B2 | 10/2017 | Bauhahn et al. |
| 9,802,038 B2 | 10/2017 | Lee et al. |

(56) References Cited

U.S. PATENT DOCUMENTS

| | | |
|---|---|---|
| 9,802,048 B2 | 10/2017 | Armstrong |
| 9,802,052 B2 | 10/2017 | Marnfeldt |
| 9,814,458 B2 | 11/2017 | North |
| 9,814,880 B2 | 11/2017 | Hershey et al. |
| 9,814,884 B2 | 11/2017 | Parker et al. |
| 9,839,786 B2 | 12/2017 | Rondoni et al. |
| 9,844,677 B2 | 12/2017 | Aghassian |
| 9,849,298 B2 | 12/2017 | Ozawa et al. |
| 9,855,436 B2 | 1/2018 | Dearden et al. |
| 9,861,812 B2 | 1/2018 | Gross et al. |
| 9,861,825 B2 | 1/2018 | Ozawa et al. |
| 9,867,989 B2 | 1/2018 | Blum et al. |
| 9,867,994 B2 | 1/2018 | Parramon |
| 9,878,158 B2 | 1/2018 | Hershey et al. |
| 9,913,980 B2 | 3/2018 | Ostroff et al. |
| 9,913,986 B2 | 3/2018 | Chow et al. |
| 9,913,990 B2 | 3/2018 | Ter-petrosyan et al. |
| 9,925,381 B2 | 3/2018 | Nassif |
| 9,929,584 B2 | 3/2018 | Aghassian et al. |
| 9,931,107 B2 | 4/2018 | Tischendorf et al. |
| 9,935,498 B2 | 4/2018 | Joshi |
| 9,943,685 B2 | 4/2018 | Ramesh et al. |
| 9,950,166 B2 | 4/2018 | Mashiach et al. |
| 9,950,173 B2 | 4/2018 | Doan |
| 9,950,179 B2 | 4/2018 | Bonde et al. |
| 9,956,419 B2 | 5/2018 | Bokil |
| 9,956,421 B2 | 5/2018 | Bunyan et al. |
| 9,974,965 B2 | 5/2018 | Perryman et al. |
| 9,981,130 B2 | 5/2018 | Lee |
| 9,993,645 B2 | 6/2018 | Walker et al. |
| 10,004,896 B2 | 6/2018 | Oron et al. |
| 10,010,717 B2 | 7/2018 | Aghassian et al. |
| 10,014,571 B2 | 7/2018 | Andersen et al. |
| 10,056,688 B2 | 8/2018 | Andersen et al. |
| 10,058,705 B2 | 8/2018 | Andersen et al. |
| 10,064,288 B2 | 8/2018 | Li et al. |
| 10,080,902 B2 | 9/2018 | Dinsmoor et al. |
| 10,105,540 B2 | 10/2018 | Oron et al. |
| 10,105,542 B2 | 10/2018 | Jiang et al. |
| 10,105,543 B2 | 10/2018 | Marnfeldt et al. |
| 10,118,040 B2 | 11/2018 | Zhu |
| 10,124,178 B2 | 11/2018 | Oron et al. |
| 10,143,845 B2 | 12/2018 | Kothandaraman |
| 10,149,976 B1 | 12/2018 | Andresen et al. |
| 10,173,062 B2 | 1/2019 | Parker |
| 10,177,609 B2 | 1/2019 | Olson et al. |
| 10,179,241 B2 | 1/2019 | Walker et al. |
| 10,182,807 B2 | 1/2019 | Bridgeman et al. |
| 10,195,425 B2 | 2/2019 | Ostroff et al. |
| 10,213,608 B2 | 2/2019 | Moffitt |
| 10,219,229 B1 | 2/2019 | Mulligan, IV |
| 10,226,637 B2 | 3/2019 | Aghassian et al. |
| 10,238,863 B2 | 3/2019 | Gross et al. |
| 10,369,366 B2 | 8/2019 | Oron et al. |
| 10,449,374 B2 | 10/2019 | Oron et al. |
| 10,532,208 B2 | 1/2020 | Ostroff et al. |
| 10,583,284 B2 | 3/2020 | Peters et al. |
| 10,653,888 B2 | 5/2020 | Oron et al. |
| 10,744,331 B2 | 8/2020 | Oron et al. |
| 10,828,181 B2 | 11/2020 | Dagan et al. |
| 2001/0044434 A1 | 11/2001 | Lee et al. |
| 2002/0016615 A1 | 2/2002 | Dev et al. |
| 2002/0026228 A1 | 2/2002 | Schauerte |
| 2002/0032468 A1 | 3/2002 | Hill |
| 2002/0055764 A1 | 5/2002 | Malonek et al. |
| 2002/0077554 A1 | 6/2002 | Schwartz et al. |
| 2002/0077556 A1* | 6/2002 | Schwartz ............. A61B 5/0031 128/903 |
| 2002/0089458 A1 | 7/2002 | Allen et al. |
| 2002/0099419 A1 | 7/2002 | Cohen et al. |
| 2002/0103454 A1 | 8/2002 | Sackner et al. |
| 2002/0120304 A1 | 8/2002 | Mest |
| 2002/0124848 A1 | 9/2002 | Sullivan et al. |
| 2002/0161377 A1 | 10/2002 | Rabkin |
| 2002/0169413 A1 | 11/2002 | Keren et al. |
| 2002/0183805 A1 | 12/2002 | Fang et al. |
| 2002/0183817 A1 | 12/2002 | Van Venrooij et al. |
| 2002/0198571 A1 | 12/2002 | Puskas |
| 2003/0014016 A1 | 1/2003 | Purdy |
| 2003/0036773 A1 | 2/2003 | Whitehurst et al. |
| 2003/0040676 A1 | 2/2003 | Prentice et al. |
| 2003/0040774 A1 | 2/2003 | Terry et al. |
| 2003/0045909 A1 | 3/2003 | Gross |
| 2003/0045914 A1 | 3/2003 | Cohen |
| 2003/0050683 A1 | 3/2003 | Boutos |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0060858 A1 | 3/2003 | Kieval et al. |
| 2003/0100933 A1 | 5/2003 | Ayal |
| 2003/0109914 A1 | 6/2003 | Westlund et al. |
| 2003/0114905 A1 | 6/2003 | Kuzma |
| 2003/0176898 A1 | 9/2003 | Gross et al. |
| 2003/0130715 A1 | 10/2003 | Boutos |
| 2003/0199806 A1 | 10/2003 | Kieval |
| 2003/0204206 A1 | 10/2003 | Padua et al. |
| 2003/0236557 A1 | 12/2003 | Whitehurst et al. |
| 2003/0236558 A1 | 12/2003 | Whitehurst et al. |
| 2004/0010303 A1 | 1/2004 | Bolea et al. |
| 2004/0015205 A1 | 1/2004 | Whitehurst et al. |
| 2004/0019364 A1 | 1/2004 | Kieval et al. |
| 2004/0019368 A1 | 1/2004 | Lattner et al. |
| 2004/0039417 A1 | 2/2004 | Soykan et al. |
| 2004/0044393 A1 | 3/2004 | Yarden |
| 2004/0048795 A1 | 3/2004 | Ivanova et al. |
| 2004/0054384 A1 | 3/2004 | Nachum |
| 2004/0064090 A1 | 4/2004 | Keren |
| 2004/0073270 A1 | 4/2004 | Firlik et al. |
| 2004/0082948 A1 | 4/2004 | Stewart et al. |
| 2004/0106954 A1 | 6/2004 | Whitehurst et al. |
| 2004/0106976 A1 | 6/2004 | Bailey et al. |
| 2004/0111006 A1 | 6/2004 | Alfemess |
| 2004/0254624 A1 | 6/2004 | Johnson |
| 2004/0133240 A1 | 7/2004 | Adams |
| 2004/0153074 A1 | 8/2004 | Bojarski et al. |
| 2004/0162590 A1 | 8/2004 | Whitehurst et al. |
| 2004/0167584 A1 | 8/2004 | Carroll et al. |
| 2004/0172094 A1 | 9/2004 | Cohen |
| 2004/0193092 A1 | 9/2004 | Deal |
| 2004/0193231 A1 | 9/2004 | David |
| 2004/0199210 A1 | 10/2004 | Shelchuk |
| 2004/0210261 A1 | 10/2004 | King et al. |
| 2004/0249431 A1 | 12/2004 | Ransbury et al. |
| 2004/0254612 A1 | 12/2004 | Ezra et al. |
| 2004/0254616 A1 | 12/2004 | Rossing et al. |
| 2005/0027346 A1 | 2/2005 | Arkusz et al. |
| 2005/0033407 A1 | 2/2005 | Weber et al. |
| 2005/0143789 A1 | 2/2005 | Whitehurst |
| 2005/0049680 A1 | 3/2005 | Fischell et al. |
| 2005/0049686 A1 | 3/2005 | Gray et al. |
| 2005/0065553 A1 | 3/2005 | Ben Ezra et al. |
| 2005/0065592 A1 | 3/2005 | Holzer |
| 2005/0090867 A1 | 4/2005 | Lapanashvili et al. |
| 2005/0096702 A1 | 5/2005 | Denker et al. |
| 2005/0096710 A1 | 5/2005 | Kieval et al. |
| 2005/0113894 A1 | 5/2005 | Zilberman et al. |
| 2005/0131495 A1 | 6/2005 | Parramon et al. |
| 2005/0143785 A1 | 6/2005 | Libbus |
| 2005/0149130 A1 | 7/2005 | Libbus |
| 2005/0149132 A1 | 7/2005 | Libbus |
| 2005/0149154 A1 | 7/2005 | Cohen |
| 2005/0149155 A1 | 7/2005 | Scheiner et al. |
| 2005/0149170 A1 | 7/2005 | Tassel et al. |
| 2005/0154418 A1 | 7/2005 | Kieval et al. |
| 2005/0165457 A1 | 7/2005 | Benser et al. |
| 2005/0182457 A1 | 8/2005 | Thrope et al. |
| 2005/0187586 A1 | 8/2005 | David |
| 2005/0197675 A1 | 9/2005 | David |
| 2005/0203610 A1 | 9/2005 | Tzeng |
| 2005/0209652 A1 | 9/2005 | Whitehurst et al. |
| 2005/0232965 A1 | 10/2005 | Falotico |
| 2005/0233962 A1 | 10/2005 | Lue et al. |
| 2005/0240229 A1 | 10/2005 | Whitehurst et al. |
| 2005/0251061 A1 | 11/2005 | Schuler et al. |

(56) References Cited

U.S. PATENT DOCUMENTS

| | | |
|---|---|---|
| 2005/0251212 A1 | 11/2005 | Kieval et al. |
| 2005/0267542 A1 | 12/2005 | David |
| 2005/0283184 A1 | 12/2005 | Gilson et al. |
| 2005/0288651 A1 | 12/2005 | VanTassel et al. |
| 2006/0004417 A1 | 1/2006 | Rossing et al. |
| 2006/0004420 A1 | 1/2006 | Rossing et al. |
| 2006/0004430 A1 | 1/2006 | Rossing et al. |
| 2006/0074453 A1 | 4/2006 | Kieval et al. |
| 2006/0085039 A1 | 4/2006 | Hastings et al. |
| 2006/0085042 A1 | 4/2006 | Hastings et al. |
| 2006/0100668 A1 | 5/2006 | Ben-David et al. |
| 2006/0111626 A1 | 5/2006 | Rossing et al. |
| 2006/0136024 A1 | 6/2006 | Cohen |
| 2006/0149124 A1 | 7/2006 | Forsell |
| 2006/0149345 A1 | 7/2006 | Boggs, II et al. |
| 2006/0155345 A1 | 7/2006 | Williams et al. |
| 2006/0167540 A1 | 7/2006 | Masters et al. |
| 2006/0173507 A1 | 8/2006 | Mrva et al. |
| 2006/0217588 A1 | 9/2006 | Gross et al. |
| 2006/0217772 A1 | 9/2006 | Libbus et al. |
| 2006/0229677 A1 | 10/2006 | Moffitt et al. |
| 2006/0259085 A1 | 11/2006 | Zhang et al. |
| 2006/0265038 A1 | 11/2006 | Hagen et al. |
| 2006/0271137 A1 | 11/2006 | Stanton-Hicks |
| 2006/0276844 A1 | 12/2006 | Alon et al. |
| 2006/0287705 A1 | 12/2006 | Weber |
| 2006/0293712 A1 | 12/2006 | Kieval et al. |
| 2007/0021673 A1 | 1/2007 | Arbel et al. |
| 2007/0021786 A1 | 1/2007 | Parnis et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027496 A1 | 2/2007 | Parnis et al. |
| 2007/0032827 A1 | 2/2007 | Katims |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049989 A1 | 3/2007 | Rossing et al. |
| 2007/0060972 A1 | 3/2007 | Kieval et al. |
| 2007/0067000 A1 | 3/2007 | Strother et al. |
| 2007/0067007 A1 | 3/2007 | Schulman |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0088397 A1 | 4/2007 | Jacobson |
| 2007/0100433 A1 | 5/2007 | Limon |
| 2007/0106340 A1 | 5/2007 | Bolea et al. |
| 2007/0142879 A1 | 6/2007 | Greenberg et al. |
| 2007/0150009 A1 | 6/2007 | Kveen et al. |
| 2007/0156179 A1 | 7/2007 | Karashurov |
| 2007/0156198 A1 | 7/2007 | Rossing et al. |
| 2007/0156201 A1 | 7/2007 | Rossing et al. |
| 2007/0167984 A1 | 7/2007 | Kieval et al. |
| 2007/0173893 A1 | 7/2007 | Pitts |
| 2007/0185540 A1 | 8/2007 | Ben-Haim et al. |
| 2007/0185542 A1 | 8/2007 | Bolea et al. |
| 2007/0185543 A1 | 8/2007 | Rossing et al. |
| 2007/0191904 A1 | 8/2007 | Libbus et al. |
| 2007/0196428 A1 | 8/2007 | Glauser et al. |
| 2007/0198064 A1 | 8/2007 | Lapanashvili et al. |
| 2007/0208392 A1 | 9/2007 | Kuschner et al. |
| 2007/0248676 A1 | 10/2007 | Stamler et al. |
| 2007/0248850 A1 | 10/2007 | Heller |
| 2007/0255369 A1 | 11/2007 | Bonde et al. |
| 2007/0255379 A1 | 11/2007 | Williams et al. |
| 2007/0276270 A1 | 11/2007 | Tran |
| 2007/0276442 A1 | 11/2007 | Haden et al. |
| 2007/0276459 A1 | 11/2007 | Rossing et al. |
| 2007/0282385 A1 | 12/2007 | Rossing et al. |
| 2007/0288076 A1 | 12/2007 | Bulkes et al. |
| 2007/0293908 A1 | 12/2007 | Cowan et al. |
| 2007/0293912 A1 | 12/2007 | Cowan et al. |
| 2007/0293927 A1 | 12/2007 | Frank et al. |
| 2008/0004535 A1 | 1/2008 | Smits |
| 2008/0004673 A1 | 1/2008 | Rossing et al. |
| 2008/0009914 A1 | 1/2008 | Buysman et al. |
| 2008/0009916 A1 | 1/2008 | Rossing et al. |
| 2008/0009917 A1 | 1/2008 | Rossing et al. |
| 2008/0021336 A1 | 1/2008 | Dobak |
| 2008/0021341 A1 | 1/2008 | Harris et al. |
| 2008/0027513 A1 | 1/2008 | Carbunaru |
| 2008/0033501 A1 | 2/2008 | Gross |
| 2008/0039915 A1 | 2/2008 | Van Den Biggelaar |
| 2008/0046016 A1 | 2/2008 | Ben-David et al. |
| 2008/0046054 A1 | 2/2008 | Hjelle et al. |
| 2008/0051767 A1 | 2/2008 | Rossing et al. |
| 2008/0051849 A1 | 2/2008 | Ben-Haim et al. |
| 2008/0058872 A1 | 3/2008 | Brockway et al. |
| 2008/0058889 A1 | 3/2008 | Ben-Haim et al. |
| 2008/0058891 A1 | 3/2008 | Ben-Haim et al. |
| 2008/0065182 A1 | 3/2008 | Strother et al. |
| 2008/0071178 A1 | 3/2008 | Greenland et al. |
| 2008/0071363 A1 | 3/2008 | Tuval et al. |
| 2008/0077016 A1 | 3/2008 | Sparks et al. |
| 2008/0077219 A1 | 3/2008 | Williams et al. |
| 2008/0082137 A1 | 4/2008 | Kieval et al. |
| 2008/0086182 A1 | 4/2008 | Ben-David |
| 2008/0091240 A1 | 4/2008 | Ben-David |
| 2008/0091241 A1 | 4/2008 | Ben-Ezra |
| 2008/0091245 A1 | 4/2008 | Ben-Ezra |
| 2008/0091255 A1 | 4/2008 | Caparso et al. |
| 2008/0097540 A1 | 4/2008 | Bolea et al. |
| 2008/0103407 A1 | 5/2008 | Bolea et al. |
| 2008/0103572 A1 | 5/2008 | Gerber |
| 2008/0109054 A1 | 5/2008 | Hastings et al. |
| 2008/0119898 A1 | 5/2008 | Ben-David |
| 2008/0119911 A1 | 5/2008 | Rosero |
| 2008/0125819 A1 | 5/2008 | Ben-David |
| 2008/0125825 A1 | 5/2008 | Ben-Ezra |
| 2008/0125827 A1 | 5/2008 | Ben-David |
| 2008/0125843 A1 | 5/2008 | Ben-David |
| 2008/0132964 A1 | 6/2008 | Cohen et al. |
| 2008/0132972 A1 | 6/2008 | Shuros et al. |
| 2008/0132983 A1 | 6/2008 | Cohen |
| 2008/0140141 A1 | 6/2008 | Ben-David |
| 2008/0140167 A1 | 6/2008 | Hagen et al. |
| 2008/0147137 A1 | 6/2008 | Cohen |
| 2008/0147168 A1 | 6/2008 | Ransbury et al. |
| 2008/0154349 A1 | 6/2008 | Rossing et al. |
| 2008/0161865 A1 | 7/2008 | Hagen et al. |
| 2008/0161887 A1 | 7/2008 | Hagen et al. |
| 2008/0161894 A1 | 7/2008 | Ben-David |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177338 A1 | 7/2008 | Ben-David |
| 2008/0177364 A1 | 7/2008 | Bolea et al. |
| 2008/0183235 A1 | 7/2008 | Stancer et al. |
| 2008/0183254 A1 | 7/2008 | Bly et al. |
| 2008/0183259 A1 | 7/2008 | Bly et al. |
| 2008/0195174 A1 | 8/2008 | Walker et al. |
| 2008/0215117 A1 | 9/2008 | Gross |
| 2008/0269740 A1 | 10/2008 | Bonde et al. |
| 2008/0275514 A1 | 11/2008 | Ben-David |
| 2008/0275524 A1 | 11/2008 | Furness et al. |
| 2009/0005859 A1 | 1/2009 | Keilman |
| 2009/0012590 A1 | 1/2009 | Inman et al. |
| 2009/0036975 A1 | 2/2009 | Ward et al. |
| 2009/0043356 A1 | 2/2009 | Longhini et al. |
| 2009/0048642 A1 | 2/2009 | Goroszeniuk |
| 2009/0062874 A1 | 3/2009 | Tracey |
| 2009/0112285 A1 | 4/2009 | Cahan et al. |
| 2009/0149912 A1 | 6/2009 | Dacey et al. |

(56) References Cited

U.S. PATENT DOCUMENTS

| | | |
|---|---|---|
| 2009/0152954 A1 | 6/2009 | Le et al. |
| 2009/0160716 A1 | 6/2009 | Rhodes et al. |
| 2009/0171425 A1 | 7/2009 | Dahlberg |
| 2009/0182402 A1 | 7/2009 | Glukhovsky |
| 2009/0198097 A1 | 8/2009 | Gross |
| 2009/0198308 A1 | 8/2009 | Gross et al. |
| 2009/0204170 A1* | 8/2009 | Hastings ............... A61N 1/057 607/33 |
| 2009/0204173 A1 | 8/2009 | Fang et al. |
| 2009/0228078 A1 | 9/2009 | Zhang et al. |
| 2009/0234407 A1 | 9/2009 | Hastings et al. |
| 2009/0248133 A1 | 10/2009 | Bloom et al. |
| 2009/0259280 A1 | 10/2009 | Wilkin et al. |
| 2009/0270951 A1 | 10/2009 | Kallmyer |
| 2009/0281594 A1 | 11/2009 | King et al. |
| 2009/0326602 A1 | 12/2009 | Glukhovsky et al. |
| 2010/0004650 A1 | 1/2010 | Ormsby et al. |
| 2010/0010290 A1 | 1/2010 | Stephens et al. |
| 2010/0010556 A1 | 1/2010 | Zhao et al. |
| 2010/0016911 A1 | 1/2010 | Willis et al. |
| 2010/0016957 A1 | 1/2010 | Jager et al. |
| 2010/0042186 A1 | 2/2010 | Ben David et al. |
| 2010/0042194 A1 | 2/2010 | Ayal |
| 2010/0049289 A1 | 2/2010 | Lund et al. |
| 2010/0052668 A1 | 3/2010 | Gleich |
| 2010/0076247 A1 | 3/2010 | Zilbershlag et al. |
| 2010/0094367 A1 | 4/2010 | Sen |
| 2010/0094373 A1 | 4/2010 | Sharma |
| 2010/0121405 A1 | 5/2010 | Ternes et al. |
| 2010/0125310 A1 | 5/2010 | Wilson et al. |
| 2010/0125313 A1 | 5/2010 | Lee et al. |
| 2010/0198298 A1 | 8/2010 | Glukovsky et al. |
| 2010/0211131 A1 | 8/2010 | Williams et al. |
| 2010/0241195 A1 | 9/2010 | Meadows et al. |
| 2010/0249875 A1 | 9/2010 | Kishawi et al. |
| 2010/0249888 A1 | 9/2010 | Glenn et al. |
| 2010/0312320 A1 | 9/2010 | Faltys et al. |
| 2010/0280568 A1 | 11/2010 | Bulkes et al. |
| 2010/0280593 A1 | 11/2010 | Richter |
| 2010/0305392 A1 | 12/2010 | Gross et al. |
| 2010/0324630 A1 | 12/2010 | Lee et al. |
| 2011/0034782 A1 | 2/2011 | Sugimachi et al. |
| 2011/0046696 A1 | 2/2011 | Barolat et al. |
| 2011/0087337 A1 | 4/2011 | Forsell |
| 2011/0093036 A1 | 4/2011 | Mashiach |
| 2011/0106237 A1 | 5/2011 | Bonsignore et al. |
| 2011/0112605 A1 | 5/2011 | Fahey |
| 2011/0118773 A1 | 5/2011 | Gross et al. |
| 2011/0137365 A1 | 6/2011 | Ben-Erza et al. |
| 2011/0137370 A1 | 6/2011 | Gross et al. |
| 2011/0152965 A1 | 6/2011 | Mashiach |
| 2011/0160792 A1 | 6/2011 | Fishel |
| 2011/0160793 A1 | 6/2011 | Gindele |
| 2011/0160798 A1 | 6/2011 | Ackermann et al. |
| 2011/0208260 A1 | 8/2011 | Jacobson |
| 2011/0208271 A1 | 8/2011 | Dobak |
| 2011/0224744 A1 | 9/2011 | Moffitt et al. |
| 2011/0224769 A1 | 9/2011 | Spenser et al. |
| 2011/0230922 A1 | 9/2011 | Fishel |
| 2011/0251660 A1 | 10/2011 | Griswold |
| 2011/0270339 A1 | 11/2011 | Murray et al. |
| 2011/0270349 A1 | 11/2011 | Cowley et al. |
| 2011/0282412 A1 | 11/2011 | Glukhovsky et al. |
| 2011/0301670 A1 | 12/2011 | Gross |
| 2011/0301760 A1 | 12/2011 | Shuster et al. |
| 2012/0003569 A1 | 1/2012 | Kawamura et al. |
| 2012/0010694 A1 | 1/2012 | Lutter et al. |
| 2012/0035679 A1 | 2/2012 | Dagan et al. |
| 2012/0035711 A1 | 2/2012 | Gross et al. |
| 2012/0041511 A1 | 2/2012 | Lee |
| 2012/0041514 A1 | 2/2012 | Gross et al. |
| 2012/0053581 A1 | 3/2012 | Wittkampf et al. |
| 2012/0065701 A1 | 3/2012 | Cauller |
| 2012/0083857 A1 | 4/2012 | Bradley et al. |
| 2012/0101326 A1 | 4/2012 | Simon et al. |
| 2012/0123498 A1 | 5/2012 | Gross |
| 2012/0130448 A1 | 5/2012 | Woods et al. |
| 2012/0130463 A1 | 5/2012 | Ben-David et al. |
| 2012/0158081 A1 | 6/2012 | Gross et al. |
| 2012/0197350 A1* | 8/2012 | Roberts ............... A61B 5/0028 607/60 |
| 2012/0215285 A1 | 8/2012 | Tahmasian et al. |
| 2012/0239107 A1 | 9/2012 | Kallmyer |
| 2012/0296389 A1 | 11/2012 | Fang et al. |
| 2012/0303112 A1 | 11/2012 | Armstrong et al. |
| 2013/0006326 A1 | 1/2013 | Ackermann et al. |
| 2013/0043736 A1 | 2/2013 | Zilbershlag |
| 2013/0066393 A1 | 3/2013 | Gross et al. |
| 2013/0123880 A1 | 5/2013 | Dagan et al. |
| 2013/0192611 A1* | 8/2013 | Taepke, II ......... A61N 1/37518 128/898 |
| 2013/0310629 A1 | 11/2013 | Lafontaine |
| 2013/0325081 A1 | 12/2013 | Karst et al. |
| 2013/0325084 A1 | 12/2013 | Lee |
| 2013/0338748 A1 | 12/2013 | Dagan |
| 2014/0025140 A1 | 1/2014 | Lui et al. |
| 2014/0031607 A1 | 1/2014 | Zilbershlag et al. |
| 2014/0081154 A1 | 3/2014 | Toth |
| 2014/0114377 A1 | 4/2014 | Dagan et al. |
| 2014/0180391 A1 | 6/2014 | Dagan et al. |
| 2014/0197786 A1 | 7/2014 | Aghassian et al. |
| 2014/0214134 A1 | 7/2014 | Peterson |
| 2014/0265620 A1 | 9/2014 | Hoarau et al. |
| 2014/0296940 A1 | 10/2014 | Gross |
| 2014/0324142 A1 | 10/2014 | Dagan et al. |
| 2015/0004709 A1 | 1/2015 | Nazarpoor |
| 2015/0005850 A1 | 1/2015 | Gross |
| 2015/0018598 A1 | 1/2015 | Nabutovsky et al. |
| 2015/0018728 A1 | 1/2015 | Gross et al. |
| 2015/0039046 A1 | 2/2015 | Gross |
| 2015/0080979 A1 | 3/2015 | Lasko et al. |
| 2015/0100109 A1 | 4/2015 | Feldman et al. |
| 2015/0148861 A1 | 5/2015 | Gross |
| 2015/0148878 A1 | 5/2015 | Yoo et al. |
| 2015/0151121 A1 | 6/2015 | Dagan et al. |
| 2015/0174406 A1 | 6/2015 | Lamensdorf et al. |
| 2015/0258339 A1 | 9/2015 | Burchiel et al. |
| 2015/0335882 A1 | 11/2015 | Gross et al. |
| 2016/0206882 A1 | 7/2016 | Oron et al. |
| 2016/0206889 A1 | 7/2016 | Plotkin et al. |
| 2016/0206890 A1 | 7/2016 | Oron et al. |
| 2016/0278951 A1 | 9/2016 | Dagan et al. |
| 2016/0361544 A1 | 12/2016 | Oron et al. |
| 2017/0007829 A1 | 1/2017 | Gross |
| 2017/0065824 A1 | 3/2017 | Dagan et al. |
| 2017/0119435 A1 | 5/2017 | Gross et al. |
| 2017/0128724 A1 | 5/2017 | Oron et al. |
| 2017/0136232 A1 | 5/2017 | Oron et al. |
| 2017/0224996 A1 | 8/2017 | Oron et al. |
| 2017/0232255 A1 | 8/2017 | Kent et al. |
| 2017/0296426 A1 | 10/2017 | Oron et al. |
| 2018/0036546 A1 | 2/2018 | Gross et al. |
| 2018/0092763 A1 | 4/2018 | Dagan et al. |
| 2018/0126157 A1 | 5/2018 | Gross et al. |
| 2018/0140849 A1 | 5/2018 | Oron et al. |
| 2018/0353764 A1 | 12/2018 | Oron et al. |
| 2019/0070420 A1 | 3/2019 | Oron et al. |
| 2019/0217085 A1 | 7/2019 | Oron et al. |
| 2020/0046974 A1 | 2/2020 | Ostroff et al. |
| 2020/0253754 A1 | 8/2020 | Dagan et al. |
| 2020/0254266 A1 | 8/2020 | Oron et al. |
| 2020/0346020 A1 | 11/2020 | Oron et al. |
| 2021/0016099 A1 | 1/2021 | Bombeck et al. |
| 2021/0128331 A1 | 5/2021 | Dagan et al. |

FOREIGN PATENT DOCUMENTS

| | | |
|---|---|---|
| CN | 101947357 | 1/2011 |
| CN | 103079497 | 5/2013 |
| CN | 203154605 | 8/2013 |
| DE | 102008054403 | 6/2010 |
| EP | 0 109 935 | 5/1984 |
| EP | 0 688 577 | 12/1995 |
| EP | 0 791 341 | 8/1997 |

(56) References Cited

FOREIGN PATENT DOCUMENTS

| | | |
|---|---|---|
| EP | 1533000 | 5/2005 |
| EP | 1703638 | 11/2012 |
| EP | 3277371 | 8/2020 |
| WO | 1998/010832 | 3/1998 |
| WO | 1999/026530 | 6/1999 |
| WO | 00/002501 | 1/2000 |
| WO | 01/10432 | 2/2001 |
| WO | 2001/010375 | 2/2001 |
| WO | 01/26729 | 4/2001 |
| WO | 02/09808 | 2/2002 |
| WO | 02/18006 | 3/2002 |
| WO | 02/26314 | 4/2002 |
| WO | 03/076008 | 9/2003 |
| WO | 03/082080 | 10/2003 |
| WO | 03/082403 | 10/2003 |
| WO | 04/014456 | 2/2004 |
| WO | 2004/064729 | 8/2004 |
| WO | 04/073484 | 9/2004 |
| WO | 05/032414 | 4/2005 |
| WO | 2005/065771 | 7/2005 |
| WO | 05/084389 | 9/2005 |
| WO | 05/097256 | 10/2005 |
| WO | 06/012033 | 2/2006 |
| WO | 06/012050 | 2/2006 |
| WO | 06/032902 | 3/2006 |
| WO | 06/041664 | 4/2006 |
| WO | 06/064503 | 6/2006 |
| WO | 06/089739 | 8/2006 |
| WO | 06/094273 | 9/2006 |
| WO | 2006/098928 | 9/2006 |
| WO | 2006/102626 | 9/2006 |
| WO | 06/123346 | 11/2006 |
| WO | 06/125163 | 11/2006 |
| WO | 07/013065 | 2/2007 |
| WO | 2007/019491 | 2/2007 |
| WO | 07/047152 | 4/2007 |
| WO | 07/064895 | 6/2007 |
| WO | 07/106533 | 9/2007 |
| WO | 07/113818 | 10/2007 |
| WO | 07/113833 | 10/2007 |
| WO | 07/114860 | 10/2007 |
| WO | 07/118090 | 10/2007 |
| WO | 2007/113883 | 10/2007 |
| WO | 07/136850 | 11/2007 |
| WO | 07/136851 | 11/2007 |
| WO | 08/039982 | 4/2008 |
| WO | 08/083120 | 7/2008 |
| WO | 08/083235 | 7/2008 |
| WO | 08/100390 | 8/2008 |
| WO | 2009/017647 | 2/2009 |
| WO | 2009/055574 | 4/2009 |
| WO | 09/095918 | 8/2009 |
| WO | 09/095920 | 8/2009 |
| WO | 2009/110935 | 9/2009 |
| WO | 10/118126 | 10/2010 |
| WO | 2011/154937 | 12/2011 |
| WO | 2012/012591 | 1/2012 |
| WO | 2012/017437 | 2/2012 |
| WO | 2012/085907 | 6/2012 |
| WO | 2013/030819 | 3/2013 |
| WO | 2013/035092 | 3/2013 |
| WO | 2013/069020 | 5/2013 |
| WO | 2013/106884 | 7/2013 |
| WO | 2013/111137 | 8/2013 |
| WO | 2013/156038 | 10/2013 |
| WO | 2013/164829 | 11/2013 |
| WO | 2014/068577 A2 | 5/2014 |
| WO | 2014/068577 A3 | 5/2014 |
| WO | 2014/081978 | 5/2014 |
| WO | 2014/087337 | 6/2014 |
| WO | 2014/167568 | 10/2014 |
| WO | 2015/004673 | 1/2015 |
| WO | 2016/028608 | 2/2016 |
| WO | 2016/157183 | 10/2016 |
| WO | 2016/172109 | 10/2016 |

OTHER PUBLICATIONS

D.W. Eisele, A.R. Schwartz, and P.L. Smith, "Tongue neuromuscular and direct hypoglossal nerve stimulation for obstructive sleep apnea.," Otolaryngologic clinics of North America, vol. 36, 2003, p. 501.

G.E. Loeb, F.J.R. Richmond, J. Singh, R.A. Peck, W. Tan, Q. Zou, and N. Sachs, "RF-powered BIONs™ for stimulation and sensing," Engineering in Medicine and Biology Society, 2004. IEMBS'04. 26th Annual International Conference of the IEEE, 2005, pp. 4182-4185.

G.E. Loeb, F.J. Richmond, and L.L. Baker, "The BION devices: injectable interfaces with peripheral nerves and muscles," Neurosurgical focus, vol. 20, 2006, pp. 1-9.

E.A. Mann, T. Burnett, S. Cornell, and C.L. Ludlow, "The effect of neuromuscular stimulation of the genioglossus on the hypopharyngeal airway," The Laryngoscope, vol. 112, 2002, pp. 351-356.

A. Oliven, R.P. Schnall G. Pillar, N. Gavriely, and M. Odeh, "Sublingual electrical stimulation of the tongue during wakefulness and sleep," Respiration physiology, vol. 127, 2001, pp. 217-226.

A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," Journal of Applied Physiology, vol. 95, 2003, p. 2023.

A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," Journal of Applied Physiology, vol. 103, 2007, p. 1662.

A.R. Schwartz, D W Eisele, A. Hari, R. Testerman, D. Erickson, and P.L. Smith, "Electrical stimulation of the lingual musculature in obstructive sleep apnea," Journal of Applied Physiology, vol. 81, 1996, p. 643.

W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," Engineering in Medicine and Biology Society, 2003. Proceedings of the 25th Annual International Conference of the IEEE, 2004, pp. 375-378.

W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," Engineering in Medicine and Biology Society, 2004. IEMBS'04. 26th Annual International Conference of the IEEE, 2005, pp. 4287-4289.

P.R. Troyk, "Injectable electronic identification, monitoring, and stimulation systems," Biomedical Engineering, vol. 1, 1999, p. 177.

T.K. Whitehurst, J.H. Schulman, K.N. Jaax, and R. Carbunaru, "The Bion® Microstimulator and its Clinical Applications," Implantable Neural Prostheses 1, 2009, pp. 253-273.

D.J. Young, "Wireless powering and data telemetry for biomedical implants," Engineering in Medicine and Biology Society, 2009. EMBC 2009. Annual International Conference of the IEEE, 2009, pp. 3221-3224.

Reid R. Harrison, et al., "Wireless Neural Recording with Single Low-Power Integrated Circuit", IEEE Trans Neural Syst Rehabil Eng. Aug. 2009; 17(4): 322-329.

An international Search Report and a Written Opinion both dated Apr. 17, 2012 which issued during the prosecution of Applicant's PCT/IL11/00870.

Patents Galore: Implantable Neurostimulators Fight Snoring and Corpse Eye-Proof Scanners. Printout from http://medgadget.com/2006/03/patents_galore.html (Downloaded Jan. 2012).

Chris Seper, "Neuros Medical Launches to Develop New Device to Block Amputee, Chronic Pain", Mar. 17, 2009.

Urgent® PC, Simple. Safe. Effective. Neuromodulation System, Uroplasty, Mar. 2009.

"JumpStart and Case Technology Ventures Invest in Neuros Medical", CTV Case Technology Ventures, Mar. 17, 2009.

(56) References Cited

OTHER PUBLICATIONS

"Responses to median and tibial nerve stimulation in patients with chronic neuropathic pain", by Theuvenet, Brain Topography, vol. 11, No. 4, 1999, pp. 305-313(9)—an abstract.
Armstrong, J, "Is electrical stimulation effective in reducing neuropathic pain in patients with diabetes?", by Foot Ankle Surg. Jul.-Aug. 1997; 36(4): 260-3—an abstract.
Ross Davis, Cerebellar Stimulation for Cerebral Palsy Spasticity, Function and Seizures. Clinical Neuroscience Center, 1999. pp. 290-299.
An Office Action dated Feb. 13, 2004, which issued during the prosecution of U.S. Appl. No. 10/254,024.
Bathien et al., Inhibition and synchronisation of tremor induced by a muscle twitch. J. Neurol, Neurosurg. and Psych. 1980, 43, 713-718.
Jobges et al., Vibratory proprioceptive stimulation affects Parkinsonian tremor. Parkinsonism & Related Disorders, 8(3), 171-176, Jan. 2002.
Mones and Weiss, The response of the tremor of patients with Parkinsonism to peripheral nerve stimulation. J. Neurol. Neurosurg. Psychiat. 1969, 32. 512-519.
Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.
N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.
M. Manfredi, "Differential Block of conduction of larger fibers in peripheral nerve by direct current", Arch. Ital. Biol. 108:52-71, 1970.
A Restriction Requirement dated May 11, 2012, which issued during the prosecution of U.S. Appl. No. 12/946,246.
Cerebral Palsy, Barry S. Russman MD, CCurrent Science Inc. 2000.
A Notice of Allowance dated Mar. 7, 2005, which issued during the prosecution of U.S. Appl. No. 10/254,024.
A Notice of Allowance dated Aug. 26, 2004, which issued during the prosecution of U.S. Appl. No. 10/254,024.
An Office Action dated Jun. 24, 2011, which issued during the prosecution of U.S. Appl. No. 12/796,102.
An International Search Report and a Written Opinion both dated Nov. 14, 2011, which issued during the prosecution of Applicant's PCT/IL2011/000440.
An International Preliminary Report on Patentability dated Dec. 10, 2012, which issued during the prosecution of Applicant's PCT/IL2011/000440.
U.S. Appl. No. 60/263,834, filed Jan. 2, 2001.
Sweeney JD et al., "An asymmetric two electrode cuff for generation of unidirectionally propagated action potentials," IEEE Transactions on Biomedical Engineering, vol. BME-33(6) (1986).
An Office Action dated Apr. 9, 2012, which issued during the prosecution of U.S. Appl. No. 12/796,102.
Invitation to pay Additional Fees dated May 10, 2013 which issued during the prosecution of Applicant's PCT/IL2013/050069.
Naples GG et al., "A spiral nerve cuff electrode for peripheral nerve stimulation," by IEEE Transactions on Biomedical Engineering, 35(11) (1988).
Sweeney JD et al., "A nerve cuff technique for selective excitation of peripheral nerve trunk regions," IEEE Transactions on Biomedical Engineering, 37(7) (1990).
Ungar IJ et al., "Generation of unidirectionally propagating action potentials using a monopolar electrode cuff," Annals of Biomedical Engineering, 14:437-450 (1986).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Rijkhoff NJ et al., "Orderly recruitment of motoneurons in an acute rabbit model," Ann. Conf. of the IEEE Eng., Medicine and Biology Soc., 20(5):2564 (1998).
Van den Honert C et al., "A technique for collision block of peripheral nerve: Frequency dependence," MP-12, IEEE Trans. Biomed. Eng. 28:379-382 (1981).
Baratta R et al., "Orderly stimulation of skeletal muscle motor units with tripolar nerve cuff electrode," IEEE Transactions on Biomedical Engineering, 36(8):836-43 (1989).
Van den Honert C et al., "Generation of unidirectionally propagated action potentials in a peripheral nerve by brief stimuli," Science, 206:1311-1312 (1979).
M. Devor, "Pain Networks", Handbook of Brand Theory and Neural Networks, ED M.A. Arbib MIT Press pp. 696-701, 1998.
Epilepsy center. http://www.bcm.tmc.edu/neural/struct/epilep/epilpsy_vagus.html.
J.F. Cortese, "Vagus Nerve Stimulation for Control of Intractable Epileptic Seizures", May 31, 2001.
Evetovich T.K. et al., Gender comparisons of the mechanomyographic responses to minimal concentric and eccentric isokinetic muscle actions, Medicine & Science in Sports & Exercise, 1998 pp. 1697-1702. Abstract.
An Office Action dated Dec. 5, 2013, which issued during the prosecution of U.S. Appl. No. 13/528,433.
An Office Action dated Sep. 30, 2013, which issued during the prosecution of U.S. Appl. No. 12/796,102.
Chow et al., Evaluation of Cardiovascular Stents as Antennas for Implantable Wireless Applications, IEEE Transactions on Microwave Theory and Techniques, vol. 57, No. 10, Oct. 2009.
Dean, J. et al., "Motor Pattern Generation", Handbook of Brain Theory and Neural Networks, pp. 696-701.
Hu et al., Percutaneous Biphasic Electrical Stimulation for Treatment of Obstructive Sleep Apnea Syndrome, IEEE Transactions on Biomedical Engineering, Jan. 2008 vol. 55 Issue:1 p. 181-187—an abstract.
A. Oliven, Electrical stimulation of the genioglossus to improve pharyngeal patency in obstructive sleep apnea: comparison of resultsobtained during sleep and anesthesia, U.S. National Library of Medicine, National Institutes of Health May 2009;148(5):315-9, 350, 349—an abstract.
U.S. Appl. No. 61/591,024, filed Jan. 26, 2012.
Mortimer et al., Peripheral Nerve and Muscle Stimulation, Neuroprosthetics Theory and Practice, Chapter 4.2, 2004, P632-638.
An Office Action dated May 19, 2017, which issued during the prosecution of U.S. Appl. No. 14/935,941.
Zabara J., Inhibition of experimental seizures in canines by repetitive vagal stimulation, Epilepsia. Nov.-Dec. 1992;33 (6):1005-12, http://www.ncbi.nlm.nih.gov/pubmed/1464256—an abstract.
A Notice of Allowance dated Jun. 9, 2014, which issued during the prosecution of U.S. Appl. No. 12/796,102.
Notice of Allowance dated Sep. 1, 2017, which issued during the prosecution of U.S. Appl. No. 14/649,873.
Brindley (1983) A technique for anodally blocking large nerve fibers.
An Office Action dated Sep. 22, 2016, which issued during the prosecution of U.S. Appl. No. 14/374,375.
DJOGlobal.com—Interferential Current Therapy (IFC).
A Notice of Allowance dated Apr. 25, 2014, which issued during the prosecution of U.S. Appl. No. 13/528,433.
U.S. Appl. No. 61/662,073, filed Jun. 20, 2012.
An Office Action dated Sep. 26, 2013, which issued during the prosecution of U.S. Appl. No. 13/528,433.
U.S. Appl. No. 60/985,353, filed Nov. 5, 2007.
An Office Action dated Apr. 4, 2017, which issued during the prosecution of U.S. Appl. No. 14/601,604.
electrotherapy.org—Interferential Therapy.
An Office Action dated Feb. 27, 2017, which issued during the prosecution of U.S. Appl. No. 14/649,873.
Lind (2012) Advances in spinal cord stimulation.
Physical Therapy Web.com—Interferential Current (IFC) Equipment.
Shealy (1967) Electrical inhibition of pain by stimulation of the dorsal columns.
Nov. 30, 2015 massdevice.com—St. Jude Medical's Proclaim Elite debuts in Europe.

(56) References Cited

OTHER PUBLICATIONS

Kaplan et al. (2009) Design and fabrication of an injection tool for neuromuscular microstimulators.
Supplementary European Search Report dated Dec. 22, 2014, which issued during the prosecution of Applicant's European App No. 11792044.7.
An Office Action dated Oct. 30, 2015, which issued during the prosecution of U.S. Appl. No. 14/226,723.
Notice of Allowance dated Jun. 15, 2017, which issued during the prosecution of U.S. Appl. No. 14/939,418.
Sinan Filiz, Luke Xie, Lee E. Weiss, O.B. Ozdoganlar, Micromilling of microbarbs for medical implants, International Journal of Machine Tools and Manufacture, vol. 48, Issues 3-4, Mar. 2008, pp. 459-472.
UCLA Team Reports Initial Success with Trigeminal Nerve Stimulation epilepsy. https://web.archive.org/web/20121020145122/https://www.epilepsy.com/epilepsy.newsletter/apr09_STIM.
Kucklick, Theodore R., ed. *The medical device R&D handbook*. Chapter 3—Intro to needles and cannulae. CRC Press, 2012.
Szmurlo, R., Starzynski, J., Wincenciak, S. and Rysz, A. (2009) 'Numerical model of vagus nerve electrical stimulation', *COMPEL—The international journal for computation and mathematics in electrical and electronic engineering*, 28(1), pp. 211-220.
An Office Action dated Apr. 5, 2017, which issued during the prosecution of U.S. Appl. No. 14/374,375.
Mitchum, A Shocking Improvement in Cardiology Science Life Blog, University of Chicago, http://sciencelife.uchospitals.edu/2010/04/13/a-shocking-improvement-in-cardiology/ (Downloaded Nov. 3, 2012).
Reggiani et al. "Biophysical effects of high frequency electrical field on muscle fibers in culture." (2009) pp. 49-56.
https://www.uroplasty.com/files/pdf/20158.pdf Brochure (Downloaded Oct. 16, 2014).
An Office Action dated Aug. 8, 2016, which issued during the prosecution of U.S. Appl. No. 14/735,741.
An International Search Report and a Written Opinion both dated Jul. 11, 2013, which issued during the prosecution of Applicant's PCT/IL2013/050069.
An International Search report and a Written Opinion both dated Apr. 29, 2014, which issued during the prosecution of Applicant's PCT/IB2013/060607.
An International Preliminary Report on Patentability dated Jul. 29, 2014, which issued during the prosecution of Applicant's PCT/IL2013/050069.
An International Preliminary Report on Patentability dated Jun. 9, 2015, which issued during the prosecution of Applicant's PCT/IB2013/060607.
An Office Action dated Dec. 12, 2016, which issued during the prosecution of U.S. Appl. No. 14/939,418.
Notice of Allowance dated Mar. 22, 2017, which issued during the prosecution of U.S. Appl. No. 14/939,418.
Injecta 2013 GmbH catalogue.
An Office Action dated Feb. 13, 2017, which issued during the prosecution of U.S. Appl. No. 14/601,604.
U.S. Appl. No. 61/733,995, filed Dec. 6, 2012.
Alo, Kenneth M., et al. "Lumbar and sacral nerve root stimulation (NRS) in the treatment of chronic pain: a novel anatomic approach and neuro stimulation technique." Neuromudulation: Technology at the Neural Interface 2.1 (1999): 23-31.
European Search Report dated Mar. 10, 2017, which issued during the prosecution of Applicant's European App No. 16196864.9.
An Office Action dated Nov. 21, 2016, which issued during the prosecution of U.S. Appl. No. 14/601,626.
Stuart, R. Morgan, and Christopher J. Winfree. "Neurostimulation techniques for painful peripheral nerve disorders." Neurosurgery Clinics of North America 20.1 (2009): 111-120.
European Search Report dated Feb. 3, 2017, which issued during the prosecution of Applicant's European App No. 16196878.9.
Gofeld, Michael, and John G. Hanlon. "Ultrasound-Guided Placement of a Paddle Lead Onto Peripheral Nerves: Surgical Anatomy and Methodology." Neuromodulation: Technology at the Neural Interface 17.1 (2014): 48-53.
An Office Action dated Dec. 6, 2017, which issued during the prosecution of U.S. Appl. No. 14/601,604.
An Office Action dated Dec. 26, 2017, which issued during the prosecution of U.S. Appl. No. 14/935,941.
An Office Action dated Jan. 8, 2018, which issued during the prosecution of U.S. Appl. No. 14/935,941.
An Office Action dated Mar. 5, 2018, which issued during the prosecution of U.S. Appl. No. 15/360,501.
An Office Action dated Nov. 30, 2017, which issued during the prosecution of U.S. Appl. No. 15/726,971.
A Notice of Allowance dated Feb. 15, 2018, which issued during the prosecution of U.S. Appl. No. 14/601,604.
A Notice of Allowance dated Jul. 16, 2018, which issued during the prosecution of U.S. Appl. No. 15/360,501.
An Office Action dated Jun. 4, 2018, which issued during the prosecution of U.S. Appl. No. 15/860,385.
Notice of Allowance dated Oct. 22, 2018, which issued during the prosecution of U.S. Appl. No. 15/860,385.
An Office Action dated Jun. 26, 2019, which issued during the prosecution of U.S. Appl. No. 15/395,257.
An Office Action dated Dec. 5, 2018, which issued during the prosecution of U.S. Appl. No. 15/581,390.
An Office Action dated Feb. 7, 2019, which issued during the prosecution of U.S. Appl. No. 15/706,956.
An Office Action dated Jul. 24, 2020, which issued during the prosecution of U.S. Appl. No. 16/363,256.
An Office Action dated Apr. 22, 2019, which issued during the prosecution of U.S. Appl. No. 15/638,924.
An Office Action dated Oct. 11, 2018, which issued during the prosecution of U.S. Appl. No. 15/638,924.
Notice of Allowance dated Jan. 17, 2020, which issued during the prosecution of U.S. Appl. No. 15/638,924.
An Interview Summary dated Mar. 5, 2019, which issued during the prosecution of U.S. Appl. No. 15/638,924.
An Advisory Action and an Interview Summary dated Sep. 16, 2019, which issued during the prosecution of U.S. Appl. No. 15/638,924.
Notice of Allowance dated Jun. 17, 2019, which issued during the prosecution of U.S. Appl. No. 15/581,390.
Notice of Allowance dated May 20, 2020, which issued during the prosecution of U.S. Appl. No. 16/183,783.
U.S. Appl. No. 61/532,660, filed Sep. 9, 2011.
Baudrie, Am J, Optimal frequency ranges for extracting information on cardiovascular autonomic control from the blood pressure and pulse interval spectrograms in mice, Physiol Regul Integr Comp Physiol 292: R904-R912, 2007.
Frost MC, Preparation and characterization of implantable sensors with nitric oxide release coatings, Microchemical Journal vol. 74 Issue: 3, Jun. 2003 pp. 277-288.
Hayashida et al., "Comparison of neurogenic contraction and relaxation in canine corpus cavemosum and penile artery and vein", J. Pharmacol. 72:231-240 (1996), p. 232 col. 2, para. 1; p. 238, col. 2, para 2.
Biosense Webster, Inc. (CA, USA) manufactures the LASSO 2515 Variable Circular Mapping Catheter, 2010.
Wustmann, "Effects of chronic baroreceptor stimulation on the autonomic cardiovascular regulation in patients with drug-resistant arterial hypertension", Hypertension 2009; 54;530-536.
Zhao et al., Loss of nitric oxide production in the coronary circulation after the development of dilated cardiomyopathy: a specific defect in the neural regulation of coronary blood flow, Clinical and Experimental Pharmacology and Physiology 23(8): 715-721 (1996).
Schoenfisch et al., "Improving the thromboresistivity of chemical sensors via nitric oxide release: fabrication and in vivo evaluation of NO-releasing oxygen-sensing catheters", Anal. Chem., 72 (6), 1119-1126, 2000.
Cheetah Medical Inc. manufactures the Cheetah Reliant, Jan. 23, 2008.

(56) References Cited

OTHER PUBLICATIONS

Paulus, "Beneficial effects of nitric oxide on cardiac diastolic function: the flip side of the coin", Heart Failure Review 5(4):337-344 (2000).
SULZER IntarTeraputic Inc. manufactures the IntraCoil® Self-Expanding Peripheral Sent (IntraCoil® Sent), Jun. 28, 2002.
Laitinen, Am J, Sympathovagal balance is major determinant of short-term blood pressure variability in healthy subjects, Physiol Heart Circ Physiol 276:1245-1252, 1999.
Kugiyama K, Nitric oxide activity is deficient in spasm arteries of patients with coronary spastic angina, Circulation 94:266-272 (1996).
Malpas, Neural influences on cardiovascular variability: possibilities and pitfalls, Am J Physiol Heart Circ Physiol 282: H6-H20, 2002.
Sherman et al., Blockade of nitric oxide synthesis reduces myocardial oxygen consumption in vivo, Circulation 95:1328-1334 (1997).
Sabbah H et al., "Global left ventricular remodeling with the Acorn Cardiac Support Device: Hemodynamic and angiographic findings in dogs with heart failure" Heart Failure Reviews 10(2):109-115 (2005) first page.
Vallais, "Heart rate and vasomotor control during exercise", Proceedings of the 29th Annual International Conference of the IEEE EMBS, CitéInternationale, Lyon, France, Aug. 23-26, 2007.
Yao Sheng-Kun, "Endogenous and exogenous nitric oxide protect against intracoronary thrombosis and reclusion after thrombolysis" Circulation. 1995;92 pp. 1005-1010.
Uemura et al., "Early short-term vagal nerve stimulation attenuates cardiac remodeling after reperfused myocardial infarction". J Card Fail. Aug. 2010;16(8):689-99.
Suga et al., Am J Physiol. Jan. 1981;240(1):H39-44.
U.S. Appl. No. 61/557,083, filed Nov. 8, 2011.
Steendijk et al., European Heart Journal (2004) 6 (Supplement D), D35-D42.
An Office Action dated Dec. 21, 2020, which issued during the prosecution of U.S. Appl. No. 16/363,256.
An Office Action dated Dec. 2, 2020, which issued during the prosecution of U.S. Appl. No. 16/166,383.
An Office Action dated May 6, 2021, which issued during the prosecution of Chinese Patent Application No. 201610957551.6.
An Office Action dated Jun. 17, 2021, which issued during the prosecution of U.S. Appl. No. 16/363,256.
An Office Action summarized English translation and Search Report dated May 6, 2021, which issued during the prosecution of Chinese Patent Application No. 201610957461.7.
An Office Action dated Jun. 1, 2021, which issued during the prosecution of Chinese Patent Application No. 201610909174.9.
An Office Action dated Aug. 13, 2021, which issued during the prosecution of Chinese Patent Application No. 201610957461.7.
U.S. Appl. No. 61/183,319, filed Jun. 2, 2009.
U.S. Appl. No. 61/331,453, filed May 5, 2010.
An International Search Report and a Written Opinion both dated Mar. 4, 2013 which issued during the prosecution of Applicant's PCT/IL2012/050452.
An Office Action dated May 16, 2018, which issued during the prosecution of U.S. Appl. No. 15/034,803.
An Office Action dated May 18, 2018, which issued during the prosecution of U.S. Appl. No. 15/354,313.
U.S. Appl. No. 60/721,728, filed Sep. 28, 2005.
U.S. Appl. No. 60/702,491, filed Jul. 25, 2005.
An International Search Report and a Written Opinion both dated Apr. 16, 2015, which issued during the prosecution of Applicant's PCT/IL2014/050972.
An Office Action dated Jan. 4, 2016, which issued during the prosecution of U.S. Appl. No. 13/741,154.
An Office Action dated May 22, 2015, which issued during the prosecution of U.S. Appl. No. 13/741,154.
An Office Action dated Sep. 18, 2015, which issued during the prosecution of U.S. Appl. No. 13/968,868.
An Office Action dated Sep. 28, 2015, which issued during the prosecution of U.S. Appl. No. 14/144,024.
An Office Action dated Sep. 15, 2015, which issued during the prosecution of U.S. Appl. No. 14/356,829.
An Office Action dated Aug. 29, 2012, which issued during the prosecution of U.S. Appl. No. 12/792,227.
An Office Action dated Jun. 19, 2012, which issued during the prosecution of U.S. Appl. No. 11/995,904.
An Office Action dated Aug. 1, 2012, which issued during the prosecution of U.S. Appl. No. 12/957,799.
An International Search Report and a Written Opinion both dated Jul. 5, 2012, which issued during the prosecution of Applicant's PCT/IL11/00952.
A Notice of Allowance dated Sep. 18, 2013, which issued during the prosecution of U.S. Appl. No. 13/210,778.
An English translation of an Office Action dated Sep. 2, 2019, which issued during the prosecution of Chinese Patent Application No. 201680022252.1.
"Stent", Free Online Medical Dictionary, pp. 1-3, accessed Jul. 17, 2013. (Year: 2013).
Cardiovascular Stents as Antennas for Implantable Wireless Applications, by Ebrish, BMEN 5151, Apr. 29, 2010.
European Search Report dated Jun. 29, 2016 which issued during the prosecution of Applicant's European App No. 12830322.9.
Extended European Search Report dated Oct. 31, 2013 which issued during the prosecution of Applicant's European App No. 11814203.3.
Web page relating to EndoSure® Wireless AAA Pressure Measurement System, manufactured by CardioMEMS, Inc. (downloaded on Nov. 30, 2010 from: http://www.cardiomems.com/content.asp?display=medical+mb&expand=ess.
An English Translation of an Office Action dated Oct. 8, 2012, which issued during the prosecution of Chinese Patent Application No. 200980111617.8.
Bucksot, Jesse E., et al. "Flat Electrode Contacts for Peripheral Nerve Stimulation." bioRxiv (2019): 593467.
"Heart rate variability," by Task Force of the European Society of Cardiology and the North American Society of Pacing and Electrophysiology, European Heart Journal (1996) 17, 354-381.
An English translation of an Office Action dated May 6, 2020, which issued during the prosecution of Chinese Patent Application No. 201680022252.1.
An Office Action dated Sep. 12, 2018, which issued during the prosecution of U.S. Appl. No. 14/486,081.
An English Summary of an Office Action dated Dec. 27, 2018, which issued during the prosecution of Chinese Patent Application No. 201680022252.1.
An English Summary of an Office Action dated Dec. 26, 2019, which issued during the prosecution of Chinese Patent Application No. 201810648157.3.
Hamilton, Coronary vascular sympathetic beta-receptor innervations,, American Journal of Physiology, vol. 230, No. 6, Jun. 1976.
Hennig et al. "Analysis of Power Absorption by Human Tissue in Deeply Implantable Medical Sensor Transponders" pp. 407-420, Advanced Microwave Circuits and Systems, Published online 01, Apr. 2010.
An Interview Summary dated May 14, 2019, which issued during the prosecution of U.S. Appl. No. 15/354,313.
An International Preliminary Report on Patentability dated Aug. 3, 2010, which issued during the prosecution of Applicant's PCT/IL09/00117.
An International Preliminary Report on Patentability dated Aug. 3, 2010, which issued during the prosecution of Applicant's PCT/IL09/00115.
An International Search Report and a Written Opinion both dated Jul. 13, 2009, which issued during the prosecution of Applicant's PCT/IL09/00117.
An International Preliminary Report on Patentability dated Jan. 29, 2008, which issued during the prosecution of Applicant's PCT/IL06/00856.
An International Preliminary Report on Patentability dated Nov. 4, 2014, which issued during the prosecution of Applicant's PCT/IL2013/050375.
An International Search Report dated Jan. 24, 2007, which issued during the prosecution of Applicant's PCT/IL06/00856.

(56) References Cited

OTHER PUBLICATIONS

An International Search Report and a Written Opinion both dated May 12, 2009, which issued during the prosecution of Applicant's PCT/IL09/00115.
An International Search Report together with the Written Opinion both dated Dec. 19, 2011, which issued during the prosecution of Applicant's PCT/IL2011/000636.
An International Search Report and a Written Opinion both dated Mar. 5, 2013, which issued during the prosecution of Applicant's PCT/IL12/00336.
An International Search Report and a Written Opinion both dated Aug. 8, 2013, which issued during the prosecution of Applicant's PCT/IL2013/050375.
Kass D., Eur Heart J. Nov. 1992;13 Suppl. E:57-64.
Katare et al. "Vagal nerve stimulation prevents reperfusion injury through inhibition of opening of mitochondrial permeability transition pore independent of the bradycardiac effect". J Thorac Cardiovasc Surg. Jan. 2009;137(1):223-31.
Kawada et al. "Vagal stimulation suppresses ischemia-induced myocardial interstitial myoglobin release". Life Sci. Sep. 26, 2008;83(13-14):490-5.
Kong et al. "Tumour necrosis factor-α and its receptors in the beneficial effects of vagal stimulation after myocardial infarction in rats". Clin Exp Pharmacol Physiol. 2011;38:300-6.
U.S. Appl. No. 61/900,461, filed Nov. 6, 2013.
An Office Action dated Mar. 13, 2012, which issued during the prosecution of U.S. Appl. No. 12/023,896.
An Office Action dated Dec. 19, 2011, which issued during the prosecution of U.S. Appl. No. 11/995,904.
An Office Action dated Nov. 18, 2009, which issued during the prosecution of U.S. Appl. No. 12/023,900.
Matheny, Vagus nerve stimulation as a method to temporarily slow or arrest the heart, Ann Thorac Surg. Jun. 1997;63(6 Suppl):S28-9. Abstract only.
Lewis, Vagus nerve stimulation decreases left ventricular contractility in vivo in the human and pig heart, J Physiol. Jul. 15, 2001; 534(Pt 2): 547-552.
An Office Action dated Aug. 9, 2011, which issued during the prosecution of U.S. Appl. No. 12/023,896.
An Office Action dated Sep. 18, 2012, which issued during the prosecution of U.S. Appl. No. 12/023,896.
An Office Action dated May 10, 2013, which issued during the prosecution of U.S. Appl. No. 12/023,896.
An Office Action dated Apr. 25, 2013, which issued during the prosecution of U.S. Appl. No. 11/995,904.
A Supplementary European Search Report dated Dec. 14, 2012, which issued during the prosecution of European Patent Application No. 06766171.
An Office Action dated Apr. 5, 2013, which issued during the prosecution of U.S. Appl. No. 12/792,227.
Takahata, "Stentenna: A Micromachined Antenna Stent for Wireless Monitoring of Implantable Microsensors" Engineering in Med. and Biol. Soci, 2003. Proceedings of the 25th Annual Intern Conference of the IEEE Sep. 17-21, 2003.
An Office Action dated Jul. 18, 2012, which issued during the prosecution of U.S. Appl. No. 13/210,778.
An Office Action dated Mar. 12, 2013, which issued during the prosecution of U.S. Appl. No. 13/210,778.
An Office Action dated Aug. 7, 2019, which issued during the prosecution of U.S. Appl. No. 15/034,803.
An Office Action dated Nov. 26, 2018, which issued during the prosecution of U.S. Appl. No. 15/034,803.
An Office Action dated Dec. 4, 2017, which issued during the prosecution of U.S. Appl. No. 15/354,313.
An Office Action dated Feb. 11, 2019, which issued during the prosecution of U.S. Appl. No. 15/354,313.
An Office Action dated Nov. 27, 2019, which issued during the prosecution of U.S. Appl. No. 15/354,313.
Notice of Allowance dated Jul. 22, 2020, which issued during the prosecution of U.S. Appl. No. 15/354,313.

Mioni et al. "Activation of an efferent cholinergic pathway produces strong protection against myocardial ischemia/reperfusion injury in rats". Crit Care Med. Nov. 2005;33(11):2621-8.
Uemura et al. "Efferent vagal nerve stimulation induces tissue inhibitor of metalloproteinase-1 in myocardial ischemia-reperfusion injury in rabbit". Am J Physiol Heart Circ Physiol. Oct. 2007;293(4):H2254-61.
Notice of Allowance dated Feb. 12, 2020, which issued during the prosecution of U.S. Appl. No. 15/034,803.
An Office Action dated Dec. 20, 2013, which issued during the prosecution of U.S. Appl. No. 12/792,227.
An Office Action dated Mar. 15, 2012, which issued during the prosecution of U.S. Appl. No. 12/792,227.
An Office Action dated Oct. 2, 2012, which issued during the prosecution of U.S. Appl. No. 12/851,214.
An Office Action dated Jan. 5, 2015, which issued during the prosecution of U.S. Appl. No. 12/959,126.
An Office Action dated Nov. 7, 2014, which issued during the prosecution of U.S. Appl. No. 13/741,154.
An Office Action dated Jan. 15, 2015, which issued during the prosecution of U.S. Appl. No. 14/356,829.
An Office Action dated Aug. 5, 2019, which issued during the prosecution of European Patent Application No. 14859833.7.
Gabriel et al. The dielectric properties of biological tissues: II. Measurements in the frequency range 10 Hz to 20 GHz, Phys. Med. Biol.41 (1996) 2251-2269.
An Office Action dated Nov. 12, 2013, which issued during the prosecution of U.S. Appl. No. 11/995,904.
An International Preliminary Report on Patentability dated Oct. 3, 2017, which issued during the prosecution of Applicant's PCT/IL2016/050338.
An Office Action dated Jan. 27, 2014, which issued during the prosecution of U.S. Appl. No. 12/023,896.
Shin Jae Ho, "Improving the biocompatibility of in vivo sensors via nitric oxide release," Analyst, 2006, 131, 609-615.
An Office Action dated Dec. 13, 2013, which issued during the prosecution of U.S. Appl. No. 13/294,062.
Taylor, The unequal influences of the left and right vagi on the control of the heart and pulmonary artery in the rattlesnake, Crotalus durissus, The Journal of Experimental Biology 212, pp. 145-151, 2009.
An interview Summary dated Jun. 30, 2020, which issued during the prosecution of U.S. Appl. No. 15/562,467.
An Advisory Action dated Aug. 10, 2020, which issued during the prosecution of U.S. Appl. No. 15/562,467.
An Office Action dated Nov. 17, 2016, which issued during the prosecution of U.S. Appl. No. 14/356,829.
An Office Action dated May 15, 2014 which issued during the prosecution of U.S. Appl. No. 12/959,126.
An Office Action dated Feb. 10, 2015, which issued during the prosecution of U.S. Appl. No. 13/968,868.
An Office Action dated Jul. 31, 2014 which issued during the prosecution of U.S. Appl. No. 13/968,868.
An Office Action dated Jul. 7, 2014 which issued during the prosecution of U.S. Appl. No. 12/792,227.
An Office Action dated Jun. 20, 2011 which issued during the prosecution of U.S. Appl. No. 12/023,896.
An International Preliminary Report on Patentability dated May 13, 2014 which issued during the prosecution of Applicant's PCT/IL2012/050452.
An Advisory Action dated Jan. 27, 2020, which issued during the prosecution of U.S. Appl. No. 15/562,467.
Levenberg, Shulamit, et al. "Endothelial cells derived from human embryonic stem cells." Proceedings of the national Academy of Sciences 99.7 (2002): 4391-4396.
European Search Report dated Mar. 31, 2015, which issued during the prosecution of Applicant's European App No. 12846947.
European Search Report dated Jun. 9, 2017, which issued during the prosecution of Applicant's European App No. 14859833.7.
An Office Action dated Apr. 29, 2020, which issued during the prosecution of U.S. Appl. No. 15/562,467.

(56) References Cited

OTHER PUBLICATIONS

An International Search Report and a Written Opinion both dated Sep. 7, 2016, which issued during the prosecution of Applicant's PCT/IL2016/050338.
An English Translation of an Office Action dated Apr. 1, 2017, which issued during the prosecution of Chinese Patent Application No. 201480072391.6.
An Office Action dated Apr. 2, 2019, which issued during the prosecution of Applicant's European App No. 16719931.4.
An Office Action dated Nov. 1, 2018, which issued during the prosecution of U.S. Appl. No. 15/562,467.
An Office Action dated Sep. 30, 2020, which issued during the prosecution of U.S. Appl. No. 15/562,467.
Notice of Allowance dated May 17, 2013, which issued during the prosecution of U.S. Appl. No. 12/851,214.
An Office Action dated Sep. 30, 2014, which issued during the prosecution of U.S. Appl. No. 12/023,896.
Notice of Allowance dated Nov. 7, 2014, which issued during the prosecution of U.S. Appl. No. 12/023,896.
An Office Action dated Jun. 7, 2012, which issued during the prosecution of U.S. Appl. No. 12/851,214.
Communication regarding a Notice of Intent to Grant dated Feb. 17, 2020, which issued during the prosecution of Applicant's European App No. 16719931.4.
An Office Action dated Jan. 25, 2019, which issued during the prosecution of U.S. Appl. No. 15/562,467.
U.S. Appl. No. 62/140,141, filed Mar. 30, 2015.
An Office Action dated Aug. 29, 2019, which issued during the prosecution of U.S. Appl. No. 15/562,467.
An English Summary of an Office Action dated Jul. 16, 2020, which issued during the prosecution of Chinese Patent Application No. 201810648157.3.

* cited by examiner

FLEXIBLE ANTENNA FOR STIMULATOR

FIELD OF THE INVENTION

Some applications of the present invention relate in general to medical implants. More specifically, some applications of the present invention relate to neurostimulator implants.

BACKGROUND

U.S. Pat. No. 8,788,045 to Gross et al., which is incorporated herein by reference, describes identifying a subject as suffering from polyneuropathy. In response to the identifying, electrodes are placed within 1 mm of a tibial nerve of the subject, the electrodes being disposed on a housing that is at least partially flexible, The electrodes are driven to treat the polyneuropathy by driving a current into the tibial nerve.

U.S. Pat. No. 9,713,707 to Oron et al. which is incorporated herein by reference, describes an electrostimulator implant that comprises (i) an implant body, the implant being injectable into tissue of a subject along a longitudinal axis of the implant body, (ii) first and second electrodes, disposed on respective first and second portions of the implant body, (iii) circuitry, disposed inside the implant body, and configured to drive the electrodes to apply current to the tissue, and (iv) a mesh, disposed over at least 50 percent of the implant body, and configured to serve as an anchor of the implant.

U.S. Pat. No. 10,124,178 to Oron et al., which is incorporated by reference, describes an implant that comprises: (a) an implant body that comprises: (i) at least a first longitudinal portion of the implant body that defines a given outer diameter; and (ii) a recessed longitudinal portion of the implant body that is radially recessed with respect to the first longitudinal portion of the implant body, such that an outer diameter of the recessed longitudinal portion is less than the outer diameter of the first longitudinal portion; and (b) a cuff coupled to the implant body around the recessed longitudinal portion of the implant body such that an outer diameter of the cuff does not exceed the outer diameter of the first longitudinal portion. The cuff defines a plurality of holes that are configured to facilitate anchoring of the implant body with respect to the subject's tissue, by facilitating tissue growth into the holes.

SUMMARY OF THE INVENTION

Applications of the present invention are directed to apparatus and methods for treating a subject using an electrostimulator implant.

Typically, the implant comprises circuitry that is electrically coupled to an antenna and to electrodes. Wireless power received using the antenna is used by the circuitry to drive the electrodes to treat the subject by applying a current to a nerve of the subject, For some applications, the antenna has a pre-treatment state and a treatment state. While the antenna is in the pre-treatment state, the antenna is not shaped to receive wireless power. While the antenna is in the treatment state, the antenna is shaped to receive wireless power, and to anchor the implant with respect to the nerve.

For some such applications, the antenna is coupled to a spring. The antenna and the spring act together as a tissue anchor that receives wireless power and that anchors the implant with respect to the nerve. Typically for such applications, expansion of the spring from a compressed state to an expanded state causes the antenna to transition from the pre-treatment state to the treatment state.

For some such applications, the antenna has a sliding end, and transition of the antenna from a non-anchoring, pre-treatment state to an anchoring, treatment state causes the sliding end to slide along the implant.

For some applications, an implant is provided that includes a housing on which the electrodes are disposed, and an anchor that includes (i) a sleeve within which a portion of the housing is disposed, (ii) a base within which a portion of the antenna is disposed, and an envelope that is openable and closable around a portion of a nerve of the subject. By closing the envelope around the nerve, the electrodes are held adjacent to the nerve.

There is therefore provided, in accordance with an application of the present invention, an apparatus including an implant, the implant including:

one or more electrodes;
circuitry that is electrically coupled to the electrodes;
a housing that houses the circuitry; and
an antenna that is electrically coupled to the circuitry, the antenna having:
 a pre-treatment state in which the antenna is not shaped to receive wireless power for treating a subject, and
 a treatment state in which the antenna is shaped to receive wireless power for treating the subject and to anchor the implant with respect to a nerve of the subject.

In an application, the apparatus includes an injector configured to house the implant and to hold the antenna in the pre-treatment state.

In an application, the housing is shaped to define a feedthrough by which the antenna is electrically coupled to the circuitry.

In an application:
the one or more electrodes include at least an anode and a cathode,
the implant defines a longitudinal axis, and
at least a portion of the antenna spans a longitudinal distance along the housing from the anode to the cathode.

In an application, the apparatus includes a spring, the spring:
coupled to the antenna,
having a compressed state and an expanded state, and
configured to cause the antenna to transition from the pre-treatment state to the treatment state by expanding from the compressed state to the expanded state.

In an application, the spring is produced by attaching a plurality of spring segments to each other.

In an application:
the implant defines a longitudinal axis,
the antenna has:
a fixed end at which the antenna is electrically coupled to the circuitry, and
a sliding end that is slidable along the longitudinal axis, with respect to the housing, and
the spring is configured to cause the antenna to transition from the pre-treatment state to the treatment state by sliding the sliding end of the antenna toward the fixed end of the antenna.

In an application, the spring and the antenna are configured to act together as a tissue anchor for anchoring the implant to tissue of the subject, the tissue anchor being configured to (i) receive wireless power, and (ii) anchor the implant with respect to the nerve.

In an application:
one of the electrodes is disposed on and rigidly coupled to the housing, and
another one of the electrodes is coupled to the tissue anchor and flexibly coupled to the housing.

There is further provided, in accordance with an application of the present invention, an apparatus for use with a nerve of a subject, the apparatus including:
an implant, the implant including:
one or more electrodes;
an antenna;
circuitry that is electrically coupled to the electrodes and (h) the antenna;
a housing that houses the circuitry; and
an anchor including (a) a base within which a portion of the antenna is disposed and (b) a sleeve, a portion of the housing disposed within the sleeve.

In an application, the housing is shaped to define a feedthrough by which the antenna is electrically coupled to the circuitry.

In an application:
the anchor is shaped to define an envelope, the envelope:
having an open state and a closed state,
configured to transition from the open state to the closed state while the implant is positioned adjacent to a portion of the nerve, such that:
while the envelope is in the open state, the implant is positionable adjacent to a portion of the nerve, and
while the envelope is in the closed state, the envelope at least partially encloses:
the portion of the nerve, and
the housing.

In an application:
the implant is shaped to define a longitudinal axis, and
the implant is positionable adjacent to the portion of the nerve such that the portion of the nerve is disposed along the longitudinal axis.

In an application, the envelope is shaped to define an arm.

In an application, a portion of the arm is coupled to the base.

In an application, a portion of the arm is coupled to an outer surface of the sleeve.

There is further provided, in accordance with an application of the present invention, a method including:
implanting an implant adjacent to a nerve of a subject, the implant including:
one or more electrodes,
circuitry that is electrically coupled to the electrodes,
a housing that houses the circuitry, and
an antenna that is electrically coupled to the circuitry, the antenna shaped in a pre-treatment state in which the antenna is not shaped to receive wireless power for treating the subject; and
causing the antenna to transition from the pre-treatment state into a treatment state in which the antenna is shaped to receive wireless power for treating the subject and to anchor the implant with respect to the nerve.

In an application:
the electrodes include at least a cathode and an anode,
the cathode is disposed on the housing,
the nerve is disposed in a vicinity of fascia having a superficial side and a deep side, and
the step of implanting includes implanting the implant such that:
the antenna is disposed on the superficial side of the fascia, and
the cathode is disposed on the deep side of the fascia.

In an application, causing the antenna to transition from the pre-treatment state into the treatment state includes expanding the antenna from a non-anchoring state into an anchoring state.

In an application:
the implant defines a longitudinal axis,
the antenna has:
a fixed end at which the antenna is electrically coupled to the circuitry, and
a sliding end; and
the step of expanding includes sliding the sliding end of the antenna along the longitudinal axis.

In an application:
the implant includes a spring, the spring:
coupled to the antenna, and
having a compressed state and an expanded state, and
causing the antenna to transition from the pre-treatment state into the treatment state includes causing the spring to expand from the compressed state to the expanded state.

In an application:
the implant defines a longitudinal axis,
the antenna has:
a fixed end at which the antenna is electrically coupled to the circuitry, and
a sliding end that is slidable along the longitudinal axis, with respect to the housing, and
causing the antenna to transition from the pre-treatment state into a treatment state includes sliding the sliding end of the antenna toward the fixed end of the antenna.

In an application:
the antenna and the spring are configured to act together as a tissue anchor for anchoring the implant to tissue of the subject,
one of the electrodes is disposed on and rigidly coupled to the housing, and
another one of the electrodes is coupled to the tissue anchor and flexibly coupled to the housing.

There is further provided, in accordance with an application of the present invention, a method, including:
implanting an implant adjacent to a nerve of a subject, the implant including:
one or more electrodes;
an antenna;
circuitry that is electrically coupled to (a) the electrodes and (b) the antenna;
a housing that houses the circuitry; and
an anchor including (a) a base within which a portion of the antenna is disposed and (b) a sleeve, a portion of the housing disposed within the sleeve, and
the step of implanting includes positioning the implant such that a base-plane defined by the base is generally parallel to a longitudinal axis defined by a portion of the nerve.

In an application:
the anchor includes an envelope, the envelope having an open state and a closed state,
the step of implanting includes:
opening the envelope into the open state, such that the step of positioning includes positioning the implant adjacent to the portion of the nerve while the envelope is in the open state, and
closing the envelope into the closed state, such that the envelope at least partially encloses:
the portion of the nerve, and
the housing.

In an application:
the envelope is shaped to define an arm,
the step of opening the envelope includes extending a portion of the arm away from the base.

In an application, the portion of the arm is a first portion of the arm, and the arm has a second portion that is coupled to the base.

In an application, the portion of the arm is a first portion of the arm, and the arm has a second portion that is coupled to an outer surface of the sleeve.

The present invention will be more fully understood from the following detailed description of applications thereof, taken together with the drawings, in which:

DETAILED DESCRIPTION OF EMBODIMENTS

Reference is made to FIGS. 1A-F and 2A-B, which are schematic illustrations showing electrostimulator implants 20, 20' and implantation thereof for treating a subject, in accordance with some applications of the invention.

Figure 1A:
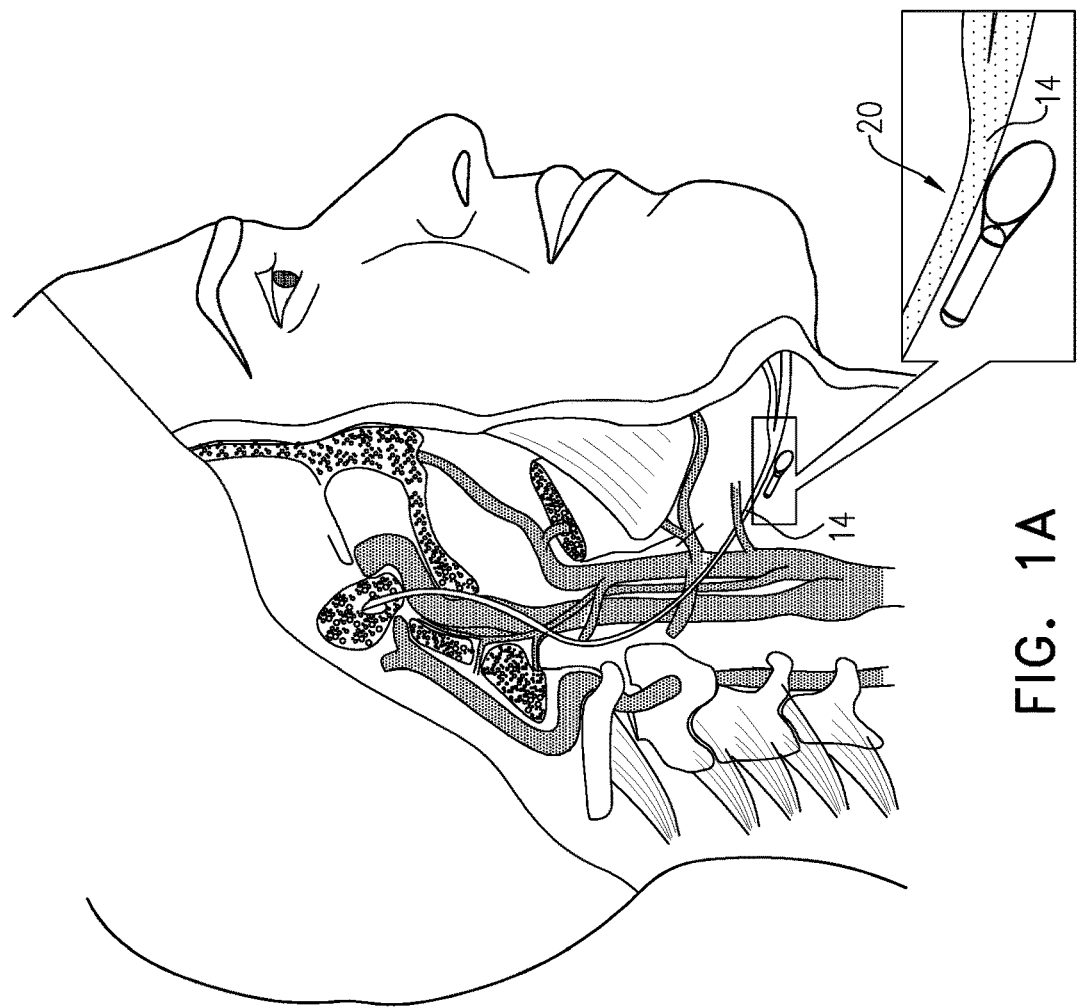
FIGS. 1A-F, 2A-B, 3A-B and 4A-B are schematic illustrations showing electrostimulator implants and implantation thereof for treating a subject, in accordance with some applications of the present invention.
Figure 1B:
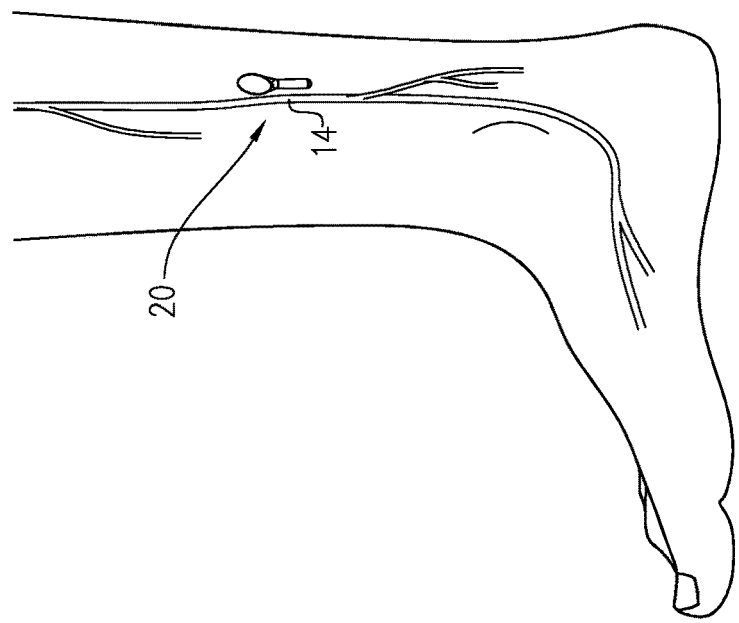

FIGS. 1A-B show implant 20 having been implanted at two exemplary implantation locations, in accordance with some applications of the invention. In each example shown, implant 20 is positioned adjacent a nerve 14 (e.g., a hypoglossal nerve in FIG. 1A, or a tibial nerve in FIG. 1B) of the subject. In this way, implant 20 may be used to provide electrostimulation to the nerve, as described hereinbelow. Typically, but not necessarily, implant 20 (e.g., a cathode 54 thereof), as well as other implants described hereinbelow, are positioned adjacent, but not touching nerve 14. In this way, care is taken to reduce application of force by the implant to the nerve.

Figure 1C:
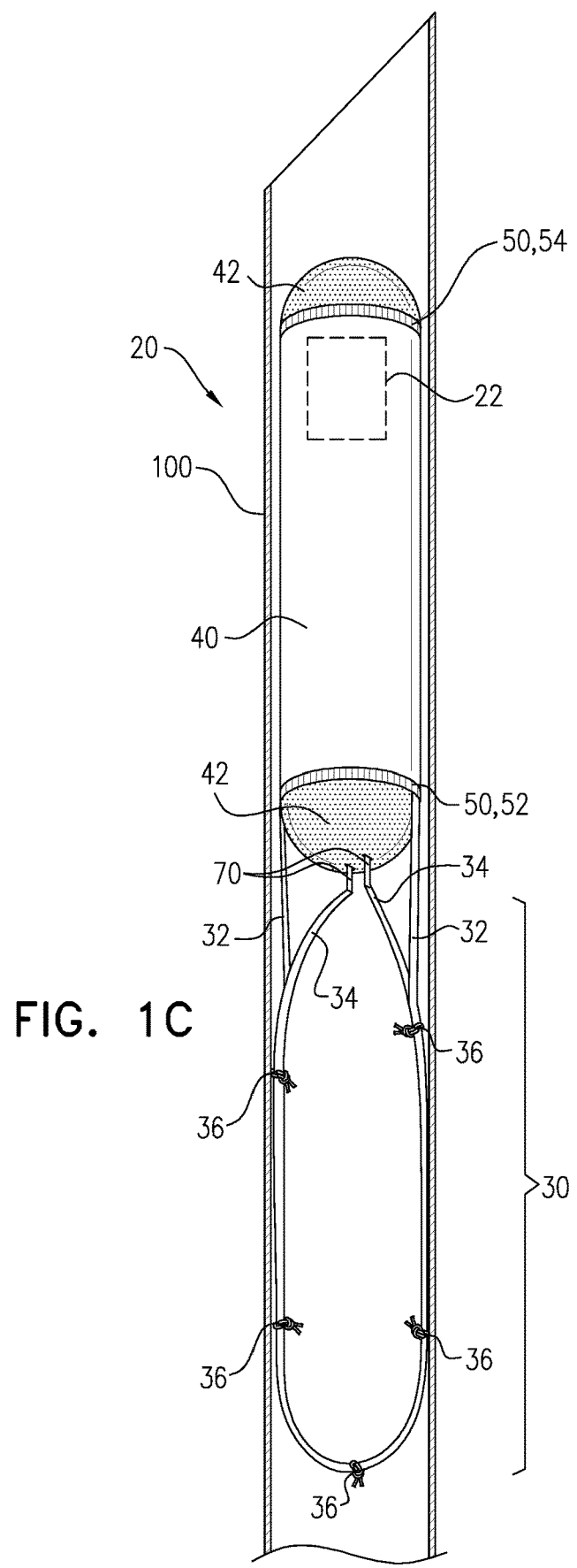
Figure 1D:
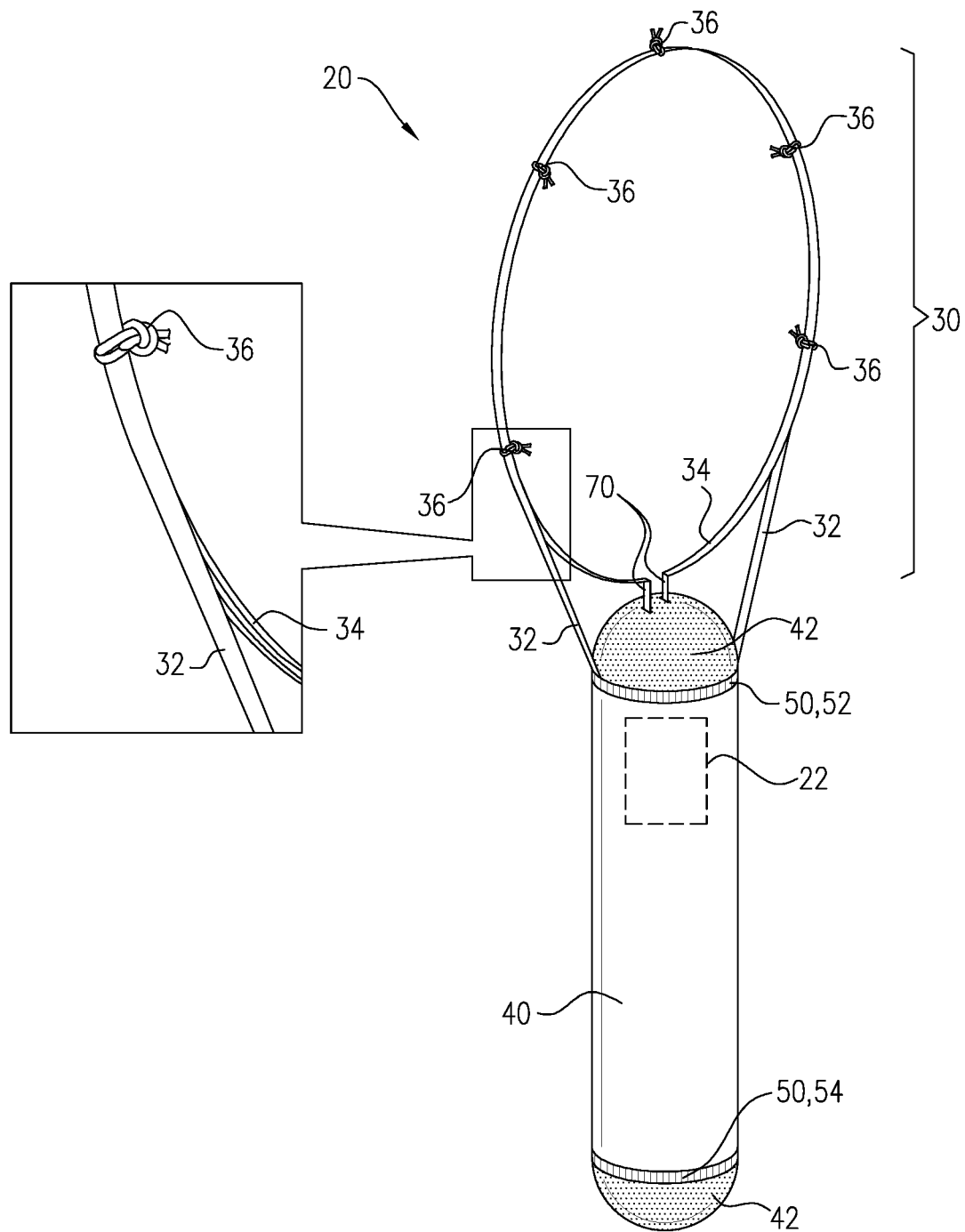

As shown in FIGS. 1C-D, implant 20 comprises one or more electrodes 50 (e.g., cathode 54 and an anode 52) and circuitry 22 that is housed within a housing 40. Circuitry 22 is typically electrically coupled to an antenna 34, e.g., via feedthroughs 70, and to electrodes 50. In this way, the wireless power that is received using antenna 34 is used by circuitry 22 to drive electrodes 50 to treat the subject by applying a current to nerve 14. Typically, antenna comprises a biocompatible, flexible, highly conductive material, e.g., gold.

For some applications, and as shown, feedthroughs 70 are disposed on a portion of housing 40 (e.g., endcap 42 thereof) that is closer to anode 52 (e.g., adjacent to the anode) than to cathode 54. Alternatively, feedthroughs may be disposed on a portion of housing 40 (e.g., endcap 42 thereof) that is closer to cathode 54 (e.g., adjacent to the cathode) than to anode 52, mutatis mutandis.

FIG. 1C shows implant 20 housed within an injector 100 that holds antenna 34 in a pre-treatment state, and FIG. 1D shows the antenna in a treatment state, after release of the implant from the injector. Typically, while antenna 34 is shaped in the pre-treatment state, the antenna is not shaped to receive wireless power for treating the subject. While antenna 34 is in the treatment state, the antenna is shaped to receive wireless power, and to anchor implant 20 with respect to nerve 14.

Although antenna 34 may be capable of receiving a certain amount of wireless power while shaped in the pre-treatment state, the antenna is capable of receiving wireless power more efficiently when the antenna is shaped in the treatment state, due to its larger receiving area. Antenna 34 may therefore be said to be shaped to receive wireless power when shaped in the treatment state.

For some applications, and as shown, antenna 34 is coupled (e.g., using sutures 36) to a spring 32. In this way, the antenna and the spring act together as a tissue anchor 30 that (i) receives wireless power and (ii) anchors implant 20 with respect to nerve 14. For some such applications, spring 32 causes the antenna to transition from the pre-treatment state to the treatment state when the spring expands (e.g., upon release from injector 100) from a compressed state to an expanded state.

Figure 1E:
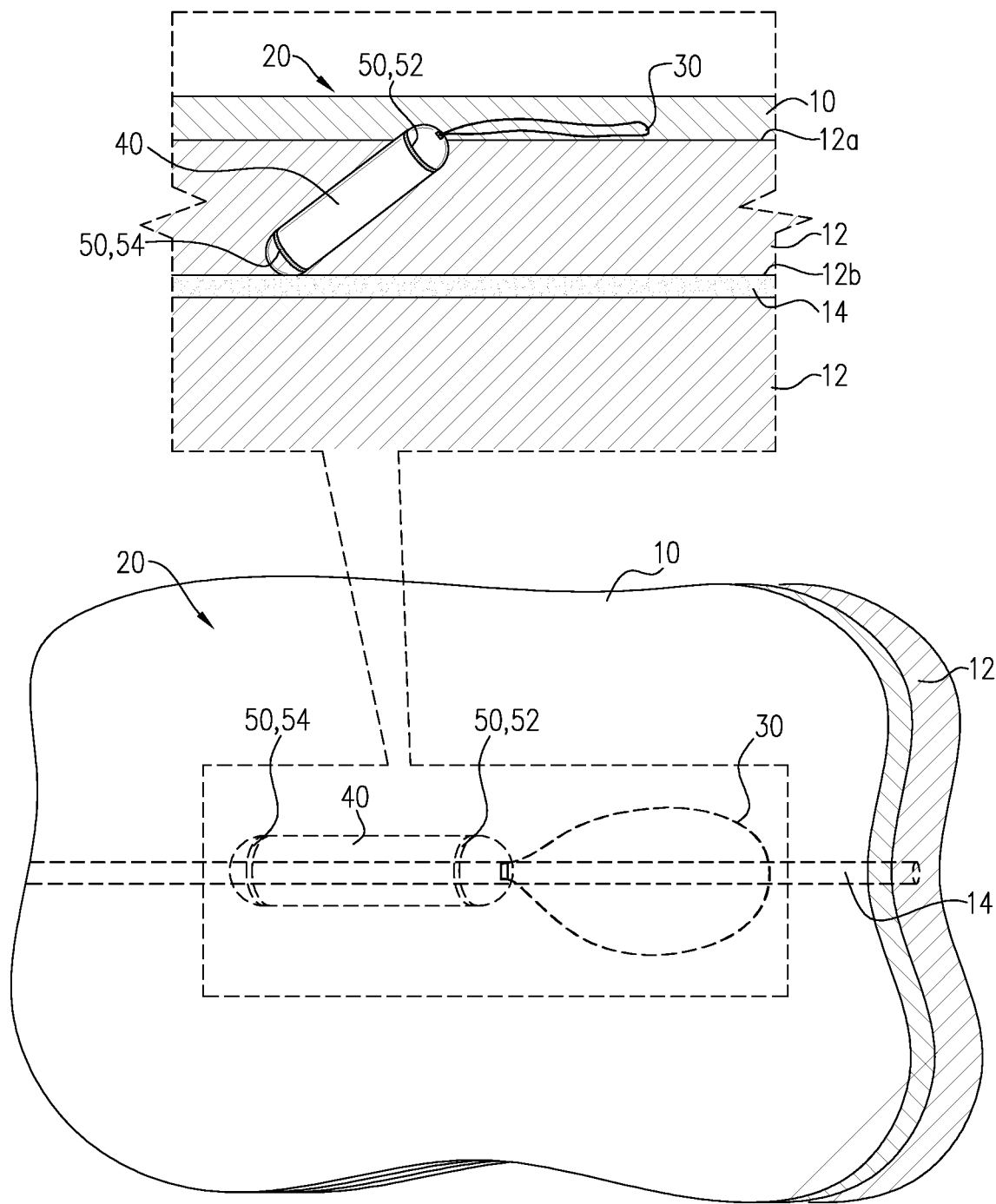
Figure 1F:
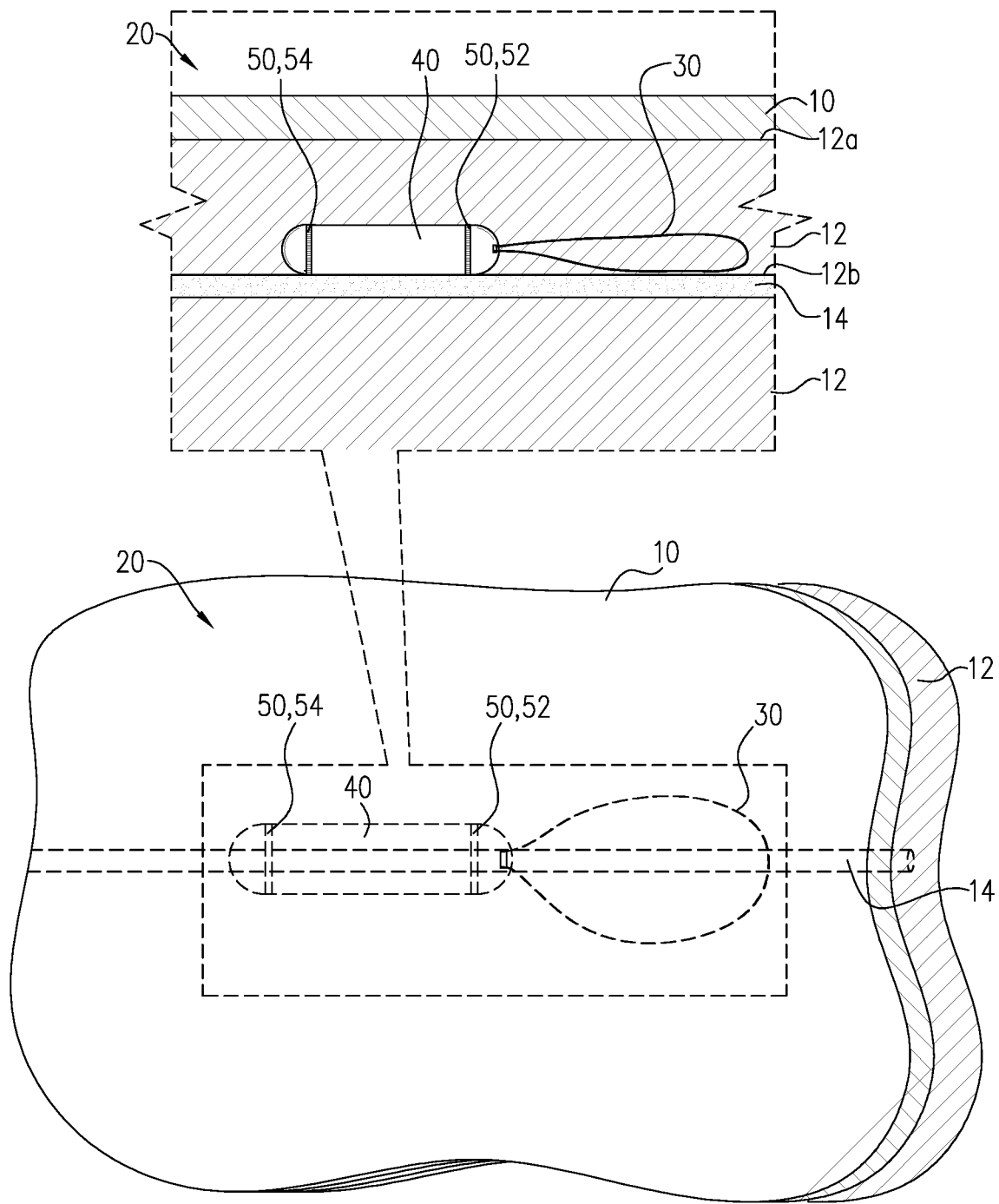

For some applications, and as shown in FIGS. 1E-F, implant 20 is implanted adjacent to nerve 14. As shown, fascia 12 has a superficial side 12a that is closer to skin 10 of the subject, and a deep side 12b that is closer to nerve 14. For the sake of clarity, other types of tissue (e.g., muscle and adipose tissue) are not shown in these schematic illustrations.

For some such applications, it may be desirable to implant the implant such that tissue anchor 30 is disposed on superficial side 12a of fascia 12 while at least one of the electrodes (e.g., cathode 54) is disposed on deep side 12b of the fascia, adjacent the nerve. For example, and as shown in FIG. 1E, a portion of housing 40 (e.g., a portion of anode 52 that is disposed on the housing) may also be disposed on superficial side 12a of fascia 12. Alternatively, both anode 52 and cathode 54 may be disposed on deep side 12b of fascia 12 (FIG. 1F) and/or generally equidistant from nerve 14.

Figure 2A:
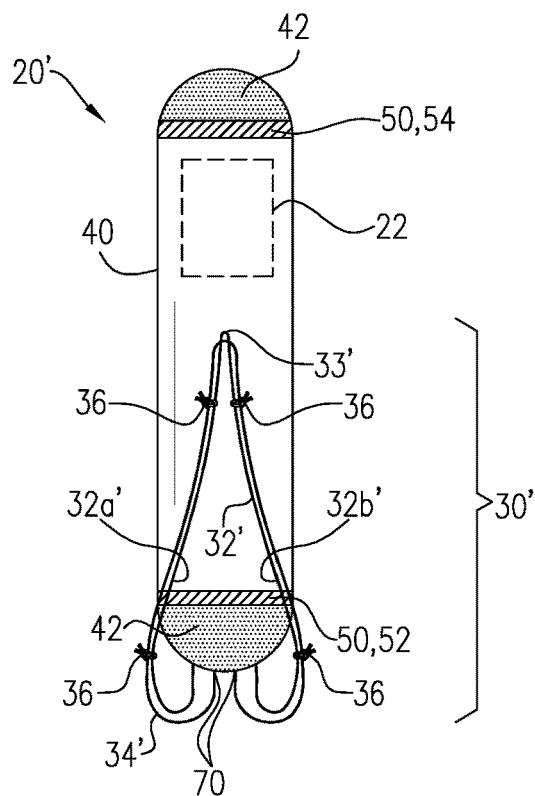
Figure 2B:
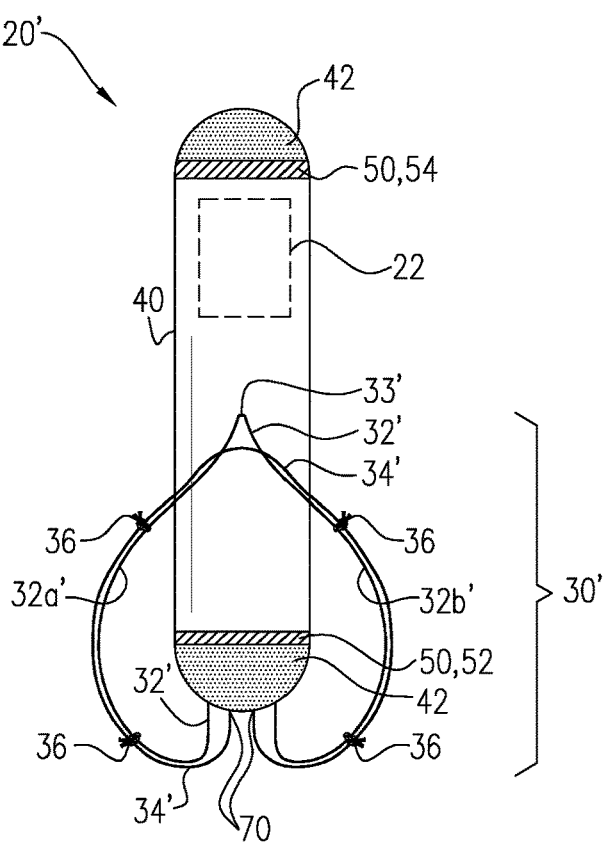

FIGS. 2A-B show an implant 20' that is generally identical to implant 20, except for tissue anchor 30'. Similarly to tissue anchor 30, tissue anchor 30' comprises an antenna 34' that is coupled (e.g., by sutures 36) to a spring 32', For some applications and as shown, spring 32' comprises a plurality of spring segments 32a', 32b'. For example and as shown, spring 32' may be assembled by attaching the spring segments (e.g., by soldering, welding, or using an adhesive adhesive) to each other at a coupling point 33' of spring 32'. In this way, when spring 32' is compressed (e.g., when implant 20' is compressed into the injector), the spring typically folds at coupling point 33', which facilitates higher compression without applying strong bending forces at a small region of the spring. When implant 20' is released from the injector, spring 32' typically expands by unfolding at coupling point 33', which increases predictability of the expansion.

Further similarly to implant 20, antenna 34' of implant 20' is typically coupled to circuitry 22 via feedthroughs 70. For some applications, and as shown, feedthroughs 70 are disposed on a portion of housing 40 (e.g., endcap 42 thereof) that is closer to anode 52 (e.g., adjacent to the anode) than to cathode 54. Alternatively, feedthroughs may be disposed on a portion of housing 40 (e.g., endcap 42 thereof) that is closer to cathode 54 (e.g., adjacent to the cathode) than to anode 52, mutatis mutandis.

Reference is made to FIGS. 3A-B and 4A-B, which are schematic illustrations showing electrostimulator implants 120, 220 and implantation thereof for treating a subject, in accordance with some applications of the invention.

Similarly to implant 20, implants 120, 220 comprise circuitry 122, 222 that is housed within a housing 140, 240. Circuitry 122 is typically electrically coupled to an antenna 134, 234, e.g., via feedthroughs 170a, 270, and to electrodes 150, 250 (e.g., to an anode 152, 252 and a cathode 154, 254).

Figure 3A:
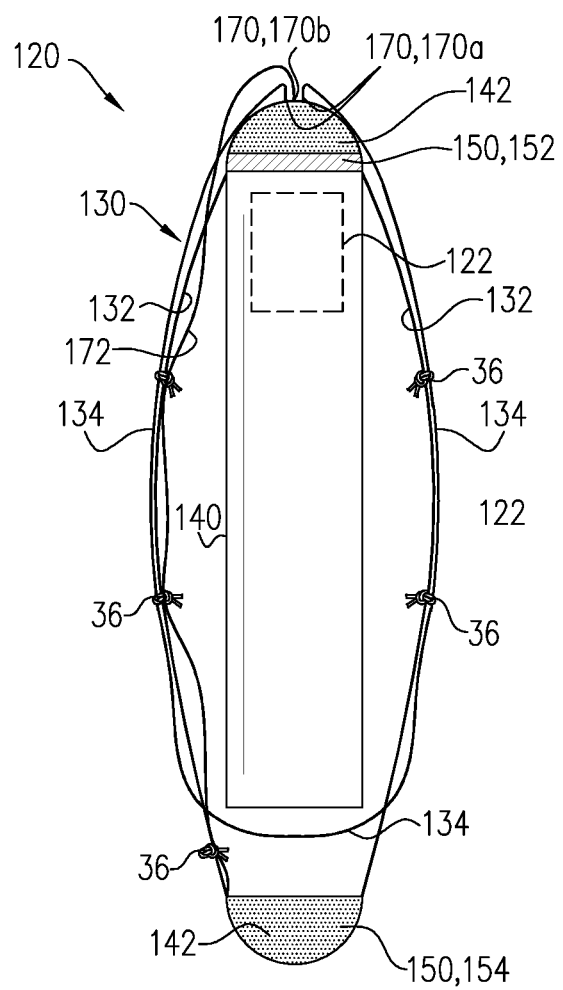
Figure 3B:
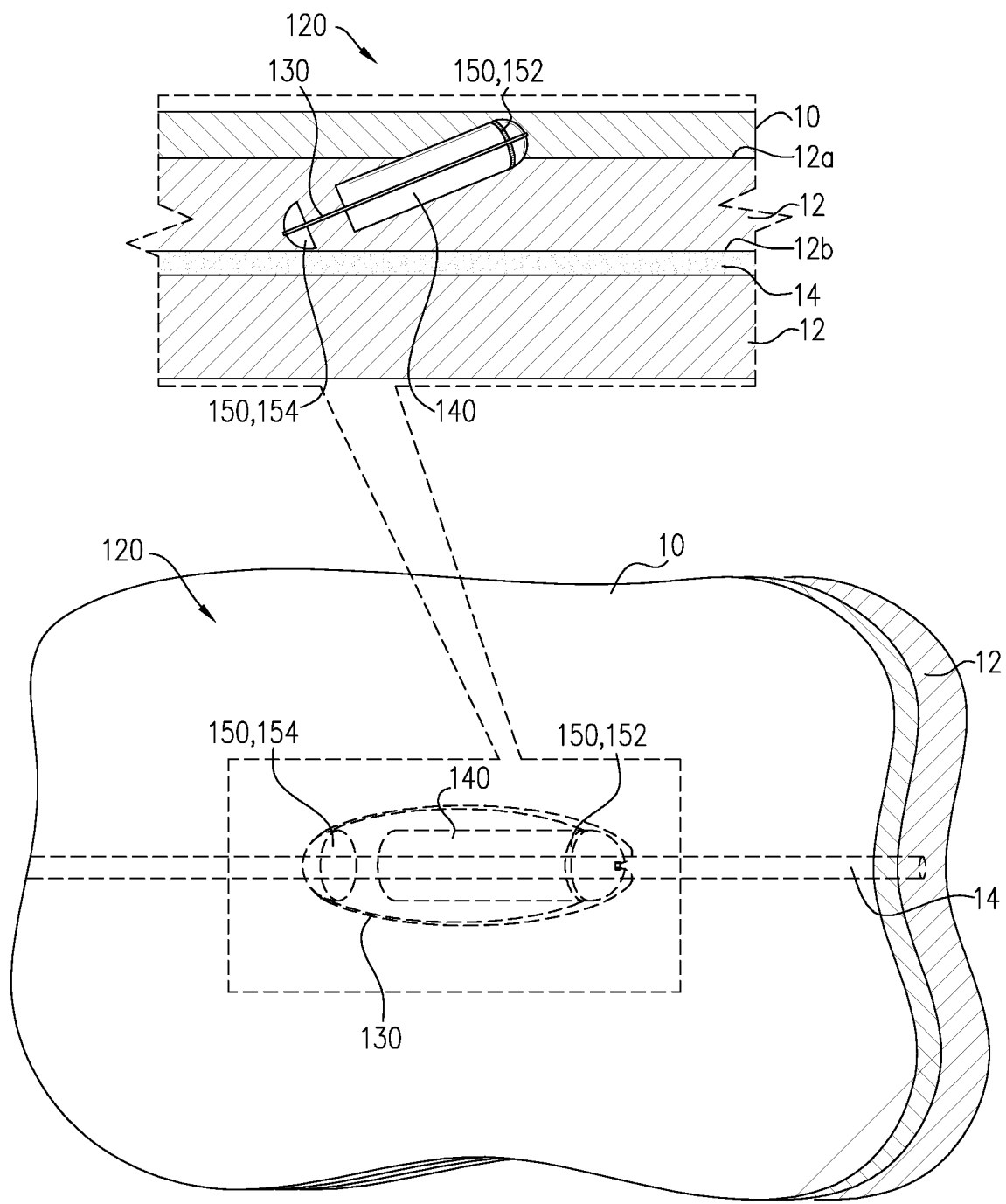
Figure 4A:
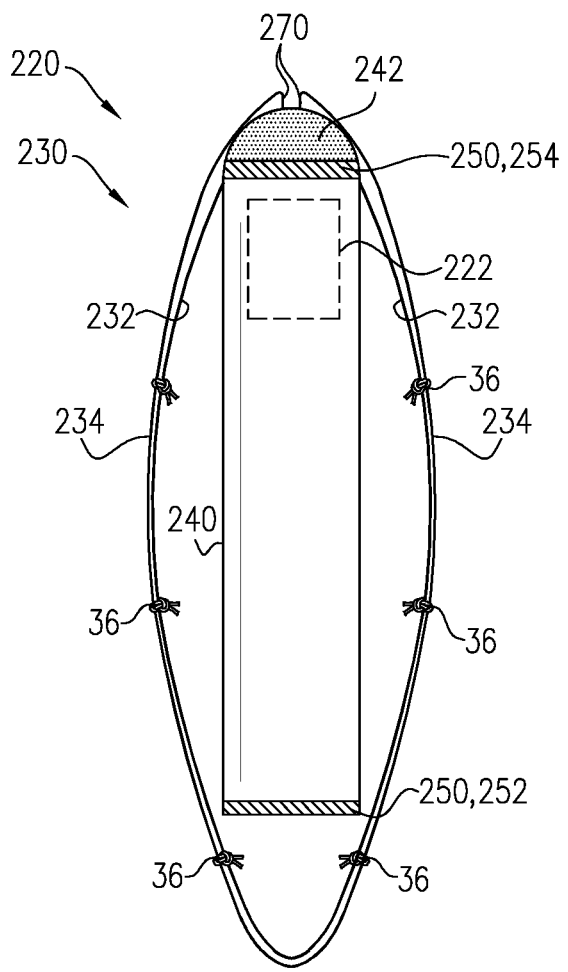
Figure 4B:
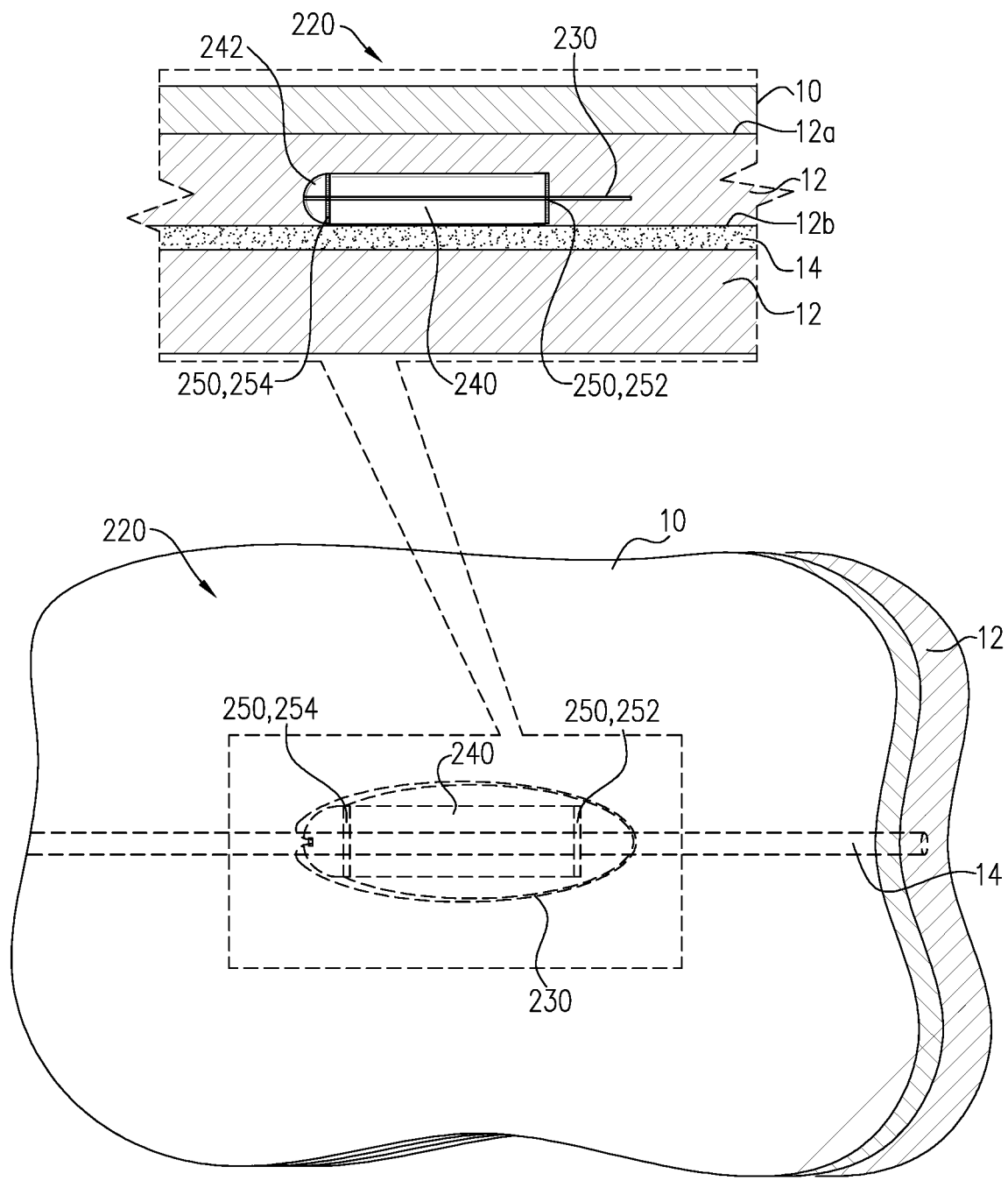

Implants 120, 220 are shown while antennas 134, 234 are in a treatment state in which antenna is shaped to receive wireless power. In this way, the wireless power that is received by antenna 134, 234 is used by circuitry 122, 222 to drive electrodes 150, 250 to treat the subject by applying a current to nerve 14. FIGS. 3B and 4B show implants 120, 220 having been implanted on deep side 12b of fascia 12, adjacent to nerve 14.

For some applications and as shown, antenna 134, 234 is coupled (e.g., using sutures 36) to a spring 132, 232. As shown, the antenna and the spring act together as a tissue anchor 130, 230 that (i) receives wireless power and (ii) anchors implant 120, 220 with respect to nerve 14.

For some applications and as shown, both antennas 134, 234 extend along a portion of housing 140, 240. For example, and as shown, at least a portion of antenna 134, 234 spans a longitudinal distance from anode 152, 252 to cathode 154, 254.

Implants 120, 220 differ from each other in terms of the location of electrodes 150. Similarly to implants 20, 20', electrodes 250 of implant 220 are both disposed on housing 240. In contrast, one electrode 150 (e.g., anode 152, as shown in FIG. 3A) is disposed on and rigidly coupled to housing 140, whereas the other electrode 150 (e.g., cathode 154, as shown) is coupled to anchor 130, e.g., on spring 132 thereof, and therefore flexibly coupled to the housing. It is hypothesized by the inventor that one of the electrodes (e.g., cathode 154, as shown) being flexibly coupled to housing 140 inhibits undesirable application of mechanical force from the electrode to nerve 14, e.g., during implantation of implant 120 or after implantation thereof.

As shown in FIG. 3A, cathode 154 is electrically coupled to circuitry 122 by wire 172, which is connected (i) to the cathode, and via a feedthrough 170b to the circuitry. In contrast to implant 120, circuitry 222 of implant 220 (FIG. 4A) is coupled to electrodes 250 from within housing 240, such that implant 220 utilizes feedthroughs 270 to connect antenna 234 to the circuitry, but does not utilize feedthroughs to couple electrodes 250 to the circuitry.

For some applications, and as shown, feedthroughs 270 are disposed on a portion of housing 240 (e.g., endcap 242 thereof) that is closer to cathode 254 (e.g., adjacent to the cathode) than to anode 252. Alternatively, feedthroughs 270 may be disposed on a portion of housing 240 (e.g., endcap 242 thereof) that is closer to anode 252 (e.g., adjacent to the anode) than to cathode 254, mutatis mutandis.

Reference is made to FIGS. 5A-B, 6A-B and 7A-B, which are schematic illustrations showing electrostimulator implants 320, 420, 420', in accordance with some applications of the invention.

Figure 5A:
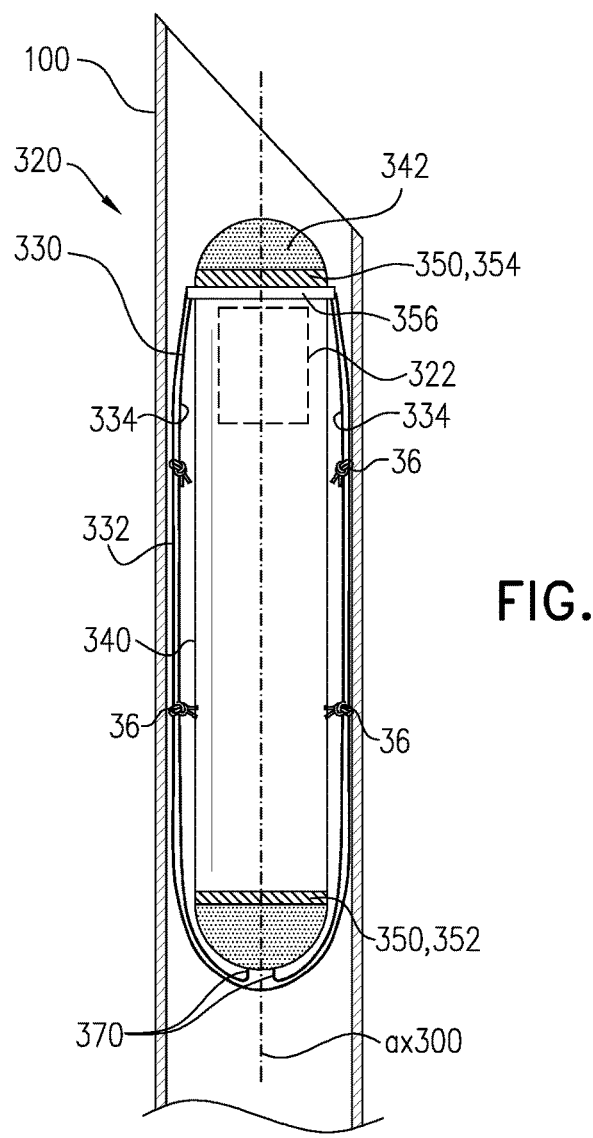
FIGS. 5A-B, 6A-B and 7A-B are schematic illustrations showing electrostimulator implants for treating a subject, in accordance with some applications of the present invention.
Figure 5B:
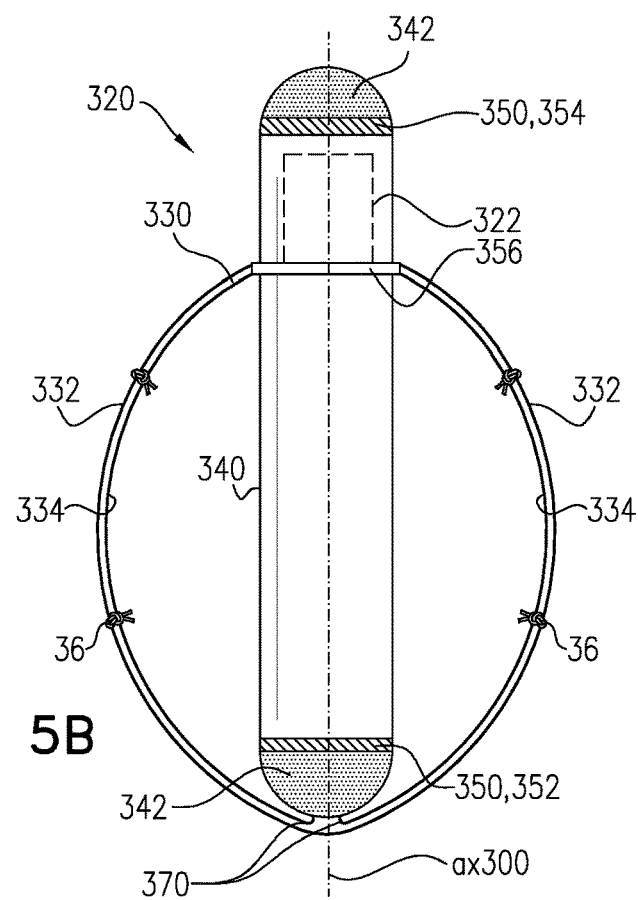
Figure 6A:
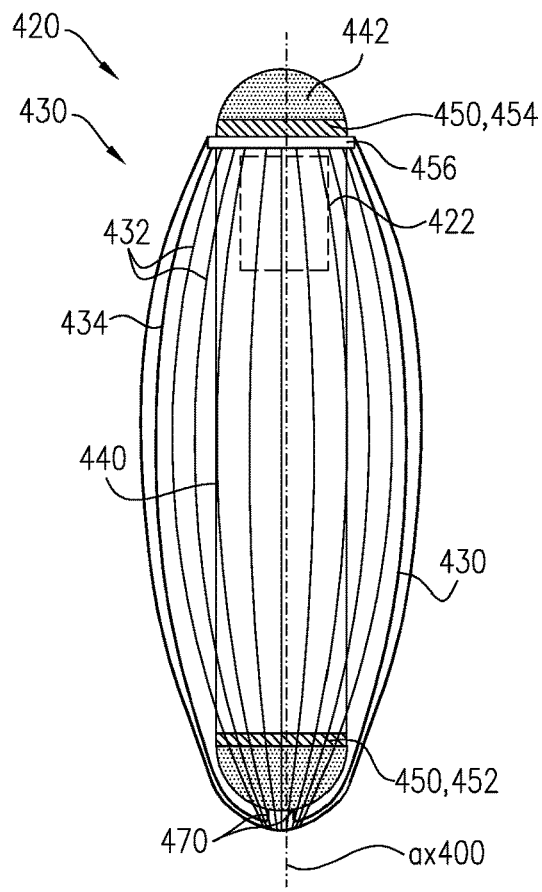
Figure 6B:
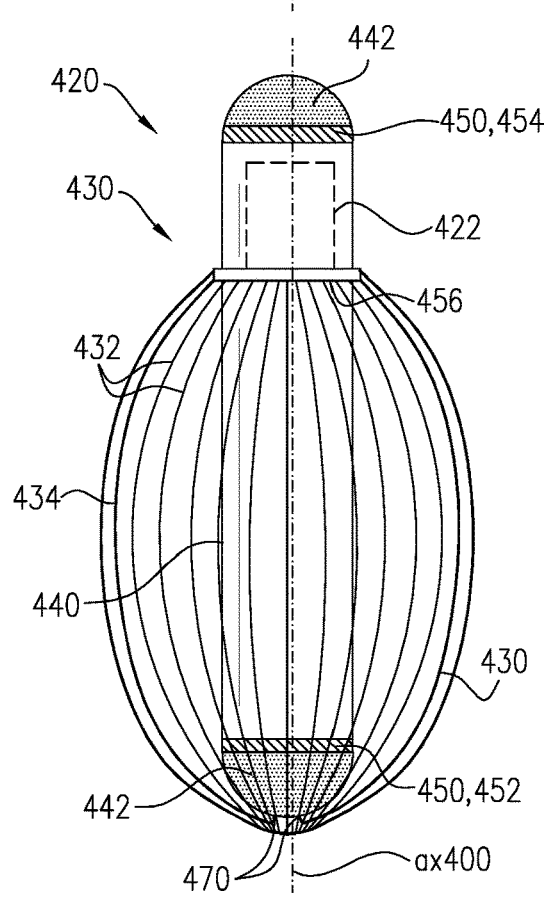
Figure 7A:
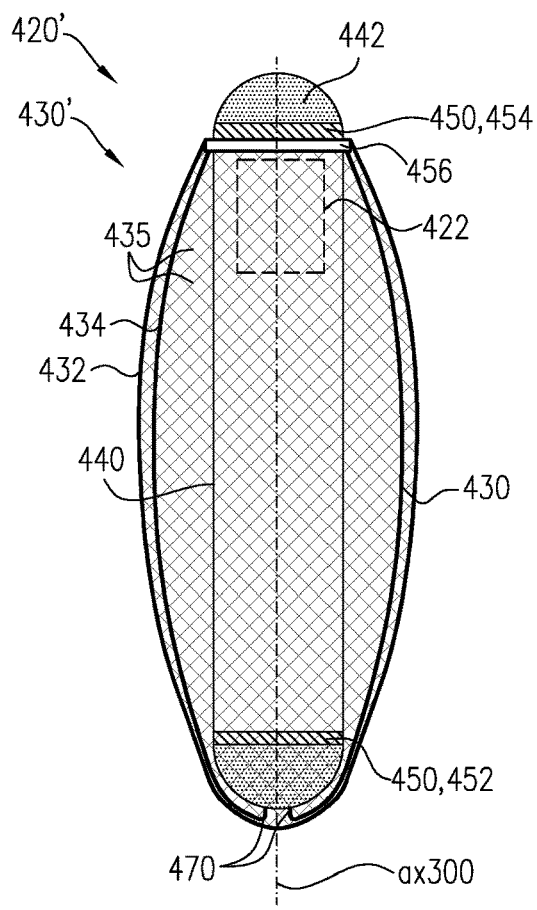
Figure 7B:
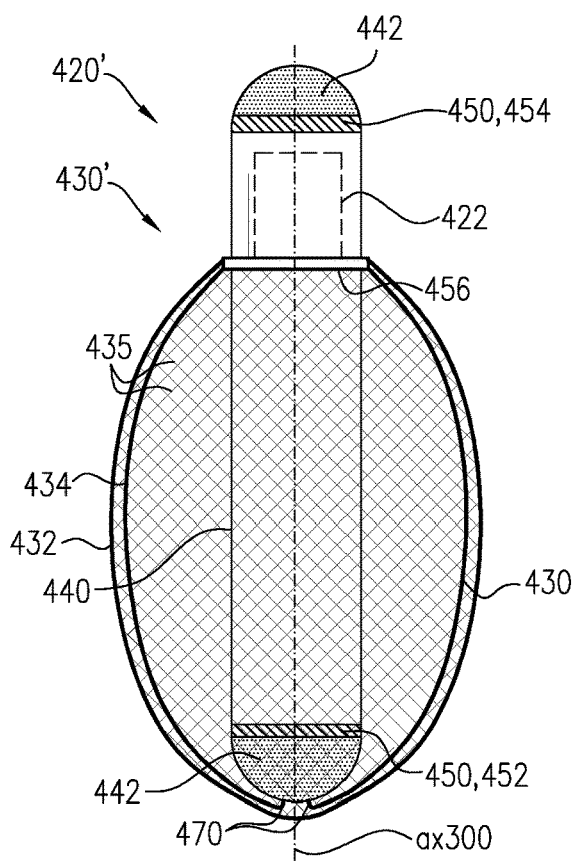

By way of illustration, FIG. 5A shows implant 320 housed within injector 100 with antenna 334 shaped in a pre-treatment state, and FIGS. 6A and 7A show implants 420, 420' having been released from the injector, with antenna 434 at a point of transition from the pre-treatment state to a treatment state (FIGS. 5B, 6B, 7B). A period of time following release from the injector (e.g., several hours, days or weeks) during which antenna 434, 434' transitions to the state shown in FIGS. 6A and 7A may be determined by several factors, including mechanical resistance that tissue surrounding the implants apply to the implants, as well as shape-memory characteristics of springs 432, 432'.

Similarly to implants 20, 120, 220, implants 320, 420, 420' comprise circuitry 322, 422 that is housed within a housing 340, 440. Circuitry 322, 422 is typically electrically coupled to an antenna 334, 434, e.g., via feedthroughs 370, 470, and to electrodes 350, 450 (e.g., to an anode 352, 452 and a cathode 354, 454, as shown). In this way, the wireless power that is received using antenna 334, 434 is used by circuitry 322, 422 to drive electrodes 350, 450 to treat the subject by applying a current to nerve 14.

As shown, and similarly to as described hereinabove with reference to implants 120, 220, antenna 334, 434 extends along a portion of housing 340. However, in contrast to the embodiments of implants 120, 220 described hereinabove, antennas 334, 434 each comprise (i) a sliding end 356, 456 that slidable along a longitudinal axis ax300, ax400 of implant 320, 420, 420', and (ii) a fixed end at which the antenna is electrically coupled to circuitry 322, 422 (e.g., via feedthroughs 370, 470).

Typically for such applications, transition of antenna 334, 434 from a non-anchoring, pre-treatment state to an anchoring, treatment state causes sliding end 356, 456 of antenna 334, 434 to slide along axis ax300, ax400. For example, sliding end 356, 456 may be a ring that surrounds and slides along housing 340, 440 with respect to electrodes 350, 450.

For some such applications and as shown, the fixed end of antenna 334, 434 is disposed at a portion of housing 340, 440 (e.g., at an endcap 342, 442 thereof) that is closed to anode 352, 452 than to cathode 354, 454. Typically for such applications, and as shown in FIGS. 5B, 6B, 7B, sliding end 356, 456 slides away from cathode 354, 454 as antenna 334, 434 expands. Alternatively, the fixed end of antenna 334, 434 may be disposed at a portion of housing 340, 440 (e.g., at endcap 342, 442 thereof) that is closed to cathode 354, 454 than to anode 352, 452, such that sliding end 356, 456 slides away from the anode as the antenna expands.

For some applications, and as shown in FIGS. 5A-B, antenna 334 may be coupled (e.g., using sutures 36) to a spring 332. In this way, antenna 334 and spring 332 act together as a tissue anchor 330 that (i) receives wireless power and (ii) anchors implant 320 with respect to nerve 14.

Implant 420 differs from implant 320 in that tissue anchor 430 typically comprises a greater number of springs 432. As shown, springs 432 of implant 420 are arranged to be generally parallel to longitudinal axis ax400. Whereas springs 432 are shown in FIG. 6B such that each spring is generally circumferentially equidistant from each other, the springs are typically sufficiently flexible such that when implant 420 is implanted into tissue, the springs may conform to the shape of the tissue due to the mechanical resistance that different types and/or layers of tissue offer. For example, flexibility of springs 432 may facilitate anchoring of implant 420 between different tissue layers (e.g., between skin 10 and fascia 12 or between the fascia and nerve 14, as shown hereinabove with respect to implants 20, 120, 220).

FIGS. 7A-7B show implant 420', which is generally similar to implant 420, with certain differences between tissue anchors 430, 430'. As shown, tissue anchor 430' comprises a flexible mesh 435. It is hypothesized by the inventor that mesh 435 may facilitate ingrowth of tissue onto the mesh, thereby further facilitating anchoring of implant 420° within the tissue (e.g., by means of fibrosis developing in the mesh).

For some applications, mesh 435 is elastic, such that the mesh, together with spring 432, causes antenna 434 to transition from the pre-treatment state to the treatment state when the mesh expands (e.g., upon release from the injector 100) from a compressed state to an expanded state.

For some applications, mesh 435 is sufficiently elastic such that expansion of the mesh alone may cause antenna 434 to transition from the pre-treatment state to the treatment state. For some such applications, implant 420 may therefore comprise mesh 435 but not spring 432.

For some applications and as shown, tissue anchor 430' comprises mesh 435 and antenna 434, which is electrically coupled to circuitry 422 through feedthroughs 470.

For some applications, antenna 434 is integrated into mesh 435, thereby obviating the discrete antenna 434 shown in FIGS. 7A-B.

Figure 8:
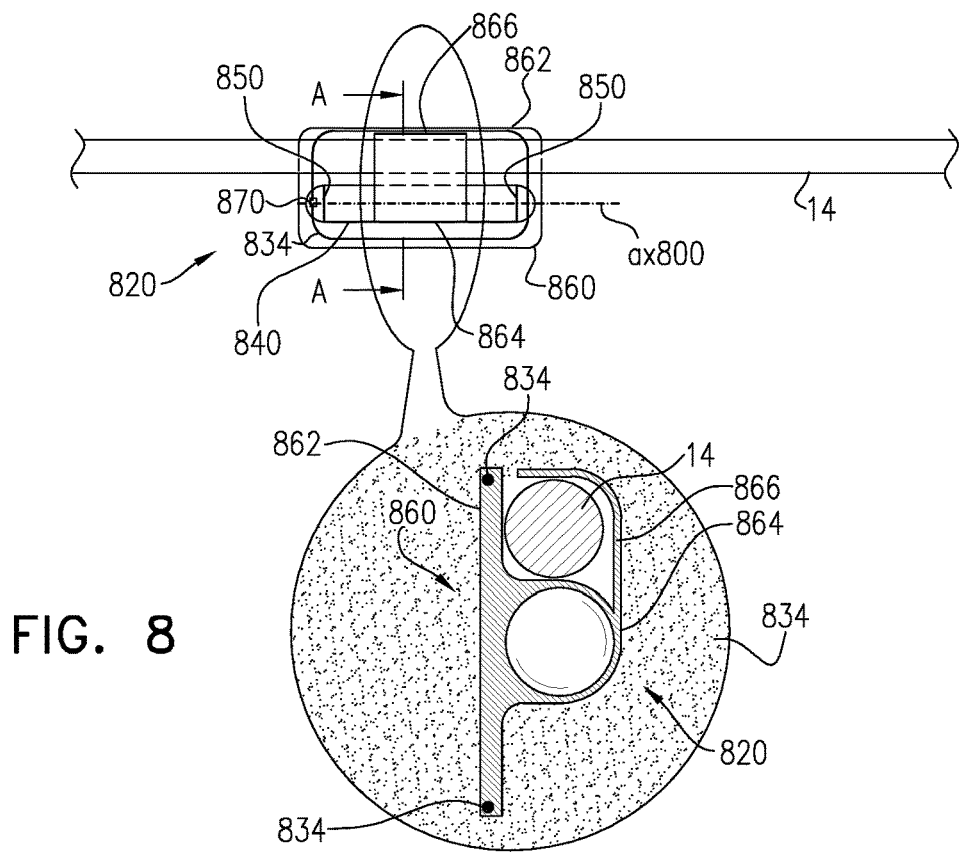
FIGS. 8-9 are schematic illustrations showing electrostimulator implants and implantation thereof for treating a subject, in accordance with some applications of the present invention.
Figure 9:
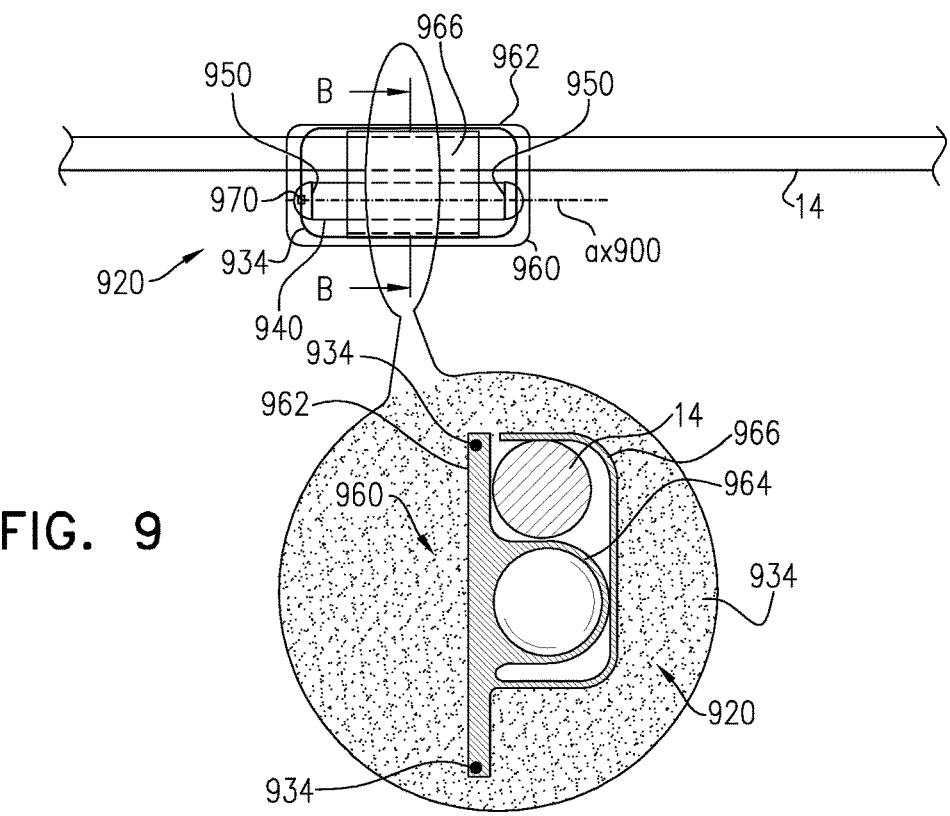

Reference is made to FIGS. 8-9, which are schematic illustrations showing electrostimulator implants 820 and 920 and implantation thereof for treating a subject, in accordance with some applications of the invention.

As shown, implants 820, 920 comprise an anchor 860, 960, as well as a housing 840, 940 on which electrodes 850, 950 are disposed. Typically, and as shown, housing 840, 940 defines a longitudinal axis ax800, ax900 along which electrodes 850, 950 are disposed.

Similarly to the implants described hereinabove, implants 820, 920 comprise circuitry (not shown) that is housed by housing 840, 940. The circuitry is electrically coupled to an antenna 834, 934 (e.g., via feedthroughs 870, 970) and to electrodes 850, 950, such that wireless power received using the antenna is used by the circuitry to drive electrodes 850, 950 to treat the subject by applying a current to nerve 14.

Typically, and as shown, anchor 860, 960 is configured to anchor the implant (e.g., electrodes 850, 950 thereof) adjacent to nerve 14. Anchor 860, 960 comprises a base 862, 962 within which a portion of antenna 834, 934 is disposed. For some applications, and as shown, most or all of a length of antenna 834, 934 is disposed within base 862, 962.

Anchor 860, 960 further comprises a sleeve 864, 964 within which a portion of housing 840, 940 is disposed. Typically, electrodes 850, 950 are not disposed within sleeve 864, 964 (or if thus disposed, are exposed to surrounding tissue through a window (not shown) in the sleeve). In this way, sleeve 864, 964 holds housing 840, 940, and therefore electrodes 850, 950 adjacent to nerve 14, yet the sleeve typically does not separate between the electrodes and the nerve, thereby facilitating application of current from the electrodes to the nerve.

For some applications, and as shown, anchor 860, 960 is shaped to define an envelope 866, 966 that has an open state and a closed state. Typically for such applications, envelope 866, 966 comprises a flexible, biocompatible material, e.g., silicone, such that the envelope may be readily opened and closed. For some such applications and as shown, envelope 866, 966 is shaped to define an arm. For example, the arm may be coupled to sleeve 864, 964 (FIGS. 8-9) and/or to base 962 (FIG. 9).

While envelope 866, 966 is open, anchor 860, 960 (e.g., a side of base 862, 962 on which sleeve 864, 964 is disposed) is positioned adjacent to a portion of nerve 14. Typically, implant 820, 920 is positioned such that a base-plane defined by base 862, 962 is generally parallel to a longitudinal axis defined by the portion of the nerve.

Envelope 866, 966 is then caused to transition (e.g., the arm is released) from the open state to the closed state, such that the envelope at least partially encloses nerve 14, and the portion of the nerve is disposed along axis ax800, ax900. (FIGS. 8-9).

It will be noted that the methods and apparatus described herein may be used in combination with those described in the following:

U.S. Pat. No. 8,788,045 to Gross et al.
U.S. Pat. No. 9,713,707 to Oron et al.
U.S. Pat. No. 10,124,178 to Oron et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an implant, the implant comprising:
   one or more electrodes;
   circuitry that is electrically coupled to the electrodes;
   a housing that houses the circuitry;
   an antenna that is electrically coupled to the circuitry, the antenna having:
      a pre-treatment state in which the antenna is not shaped to receive wireless power for treating a subject, and
      a treatment state in which the antenna is shaped to receive wireless power for treating the subject and to anchor the implant with respect to a nerve of the subject; and
   a spring, the spring:
      coupled to the antenna,
      having a compressed state and an expanded state, and
      configured to cause the antenna to transition from the pre-treatment state to the treatment state by expanding from the compressed state to the expanded state,
   wherein:
      the implant defines a longitudinal axis,
      the antenna has:
         a fixed end at which the antenna is electrically coupled to the circuitry, and
         a sliding end that is slidable along the longitudinal axis, with respect to the housing, and
      the spring is configured to cause the antenna to transition from the pre-treatment state to the treatment state by sliding the sliding end of the antenna toward the fixed end of the antenna.

2. The apparatus according to claim 1, further comprising an injector configured to house the implant and to hold the antenna in the pre-treatment state.

3. The apparatus according to claim 1, wherein the housing is shaped to define a feedthrough by which the antenna is electrically coupled to the circuitry.

4. The apparatus according to claim 1, wherein:
   the one or more electrodes comprise at least an anode and a cathode,
   and
   at least a portion of the antenna spans a longitudinal distance along the housing from the anode to the cathode.

5. The apparatus according to claim 1, wherein the spring and the antenna are configured to act together as a tissue anchor for anchoring the implant to tissue of the subject, the tissue anchor being configured to (i) receive wireless power, and (ii) anchor the implant with respect to the nerve.

6. A method comprising:
implanting an implant adjacent to a nerve of a subject, the implant defining a longitudinal axis, and including:
one or more electrodes,
circuitry that is electrically coupled to the electrodes,
a housing that houses the circuitry, and
an antenna that is electrically coupled to the circuitry, the antenna:
shaped in a pre-treatment state in which the antenna is not shaped to receive wireless power for treating the subject, and
having:
a fixed end at which the antenna is electrically coupled to the circuitry, and
a sliding end; and
causing the antenna to transition from the pre-treatment state into a treatment state in which the antenna is shaped to receive wireless power for treating the subject and to anchor the implant with respect to the nerve by:
expanding the antenna from a non-anchoring state into an anchoring state, and
sliding the sliding end of the antenna along the longitudinal axis.

7. The method according to claim 6, wherein:
the implant further comprises a spring, the spring:
coupled to the antenna, and
having a compressed state and an expanded state,
the step of expanding comprises expanding the antenna from the non-anchoring state into the anchoring state by causing the spring to expand from the compressed state to the expanded state, and
the step of sliding comprises sliding the end of the antenna along the longitudinal axis by causing the spring to expand from the compressed state to the expanded state.

8. The method according to claim 7, wherein:
the antenna has:
a fixed end at which the antenna is electrically coupled to the circuitry, and
a sliding end that is slidable along the longitudinal axis, with respect to the housing, and
the step of sliding comprises sliding the end of the antenna along the longitudinal axis by sliding the sliding end of the antenna toward the fixed end of the antenna.

9. A method comprising:
implanting an implant adjacent to a nerve of a subject, the implant defining a longitudinal axis, and including:
one or more electrodes,
circuitry that is electrically coupled to the electrodes,
a housing that houses the circuitry,
an antenna that is electrically coupled to the circuitry, the antenna:
shaped in a pre-treatment state in which the antenna is not shaped to receive wireless power for treating the subject, and
having:
a fixed end at which the antenna is electrically coupled to the circuitry, and
a sliding end that is slidable along the longitudinal axis,
with respect to the housing,
a spring, the spring:
coupled to the antenna, and
having a compressed state and an expanded state; and
causing the antenna to transition from the pre-treatment state into a treatment state in which the antenna is shaped to receive wireless power for treating the subject and to anchor the implant with respect to the nerve, by:
causing the spring to expand from the compressed state to the expanded state; and
sliding the sliding end of the antenna toward the fixed end of the antenna.

* * * * *